(12) United States Patent
Bae et al.

(10) Patent No.: US 9,388,165 B2
(45) Date of Patent: Jul. 12, 2016

(54) ISOQUINOLINE-5-CARBOXAMIDE DERIVATIVE HAVING INHIBITORY ACTIVITY FOR PROTEIN KINASE

(71) Applicant: HANMI PHARM. CO., LTD., Hwaseong-si, Gyeonggi-do (KR)

(72) Inventors: In Hwan Bae, Hwaseong-si (KR); Sang Mi Han, Seoul (KR); Eun Joo Kwak, Seogwipo-si (KR); Young Gil Ahn, Seongnam-si (KR); Kwee Hyun Suh, Suwon-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 14/413,305

(22) PCT Filed: Jul. 17, 2013

(86) PCT No.: PCT/KR2013/006392
§ 371 (c)(1),
(2) Date: Jan. 7, 2015

(87) PCT Pub. No.: WO2014/014270
PCT Pub. Date: Jan. 23, 2014

(65) Prior Publication Data
US 2015/0191450 A1    Jul. 9, 2015

(30) Foreign Application Priority Data
Jul. 19, 2012 (KR) .................... 10-2012-0078904

(51) Int. Cl.
| C07D 217/12 | (2006.01) |
| C07D 401/12 | (2006.01) |
| A61K 31/472 | (2006.01) |
| C07D 217/22 | (2006.01) |
| C07D 217/02 | (2006.01) |

(52) U.S. Cl.
CPC ............ C07D 401/12 (2013.01); C07D 217/02 (2013.01); C07D 217/22 (2013.01)

(58) Field of Classification Search
None
See application file for complete search history.

(56) References Cited

FOREIGN PATENT DOCUMENTS

| WO | 99/32455 A1 | 7/1999 |
| WO | 01/66540 A1 | 9/2001 |
| WO | 02/100405 A1 | 12/2002 |
| WO | 03/022832 A1 | 3/2003 |
| WO | 03/022837 A1 | 3/2003 |
| WO | 2005105777 A1 | 11/2005 |
| WO | 2005/115986 A1 | 12/2005 |
| WO | WO 2005115972 A1 * | 12/2005 |
| WO | 2011/093684 A2 | 8/2011 |

OTHER PUBLICATIONS

International Searching Authority, International Search Report for PCT/KR2013/006392 dated Oct. 31, 2013 [PCT/ISA/210].
European Patent Office, Communication dated Dec. 3, 2015 issued in counterpart European Application No. 13819868.4.
European Patent Office, Communication dated Mar. 4, 2015, issued in counterpart European Application No. 13819868.4.

* cited by examiner

*Primary Examiner* — Zinna Northington Davis
(74) *Attorney, Agent, or Firm* — Sughrue Mion, PLLC

(57) ABSTRACT

A compound selected from the group consisting of an isoquinoline-5-carboxamide derivative of formula (I), a pharmaceutically acceptable salt, an isomer, a hydrate and a solvate thereof is effective for the prevention or treatment of diseases associated with abnormal cell growth, which are caused by abnormal activation of a protein kinases.

13 Claims, No Drawings

ISOQUINOLINE-5-CARBOXAMIDE DERIVATIVE HAVING INHIBITORY ACTIVITY FOR PROTEIN KINASE

CROSS REFERENCE TO RELATED APPLICATIONS

This application is a National Stage of International Application No. PCT/KR2013/006392 filed Jul. 17, 2013, claiming priority based on Korean Patent Application No. 10-2012-0078904 filed Jul. 19, 2012, the contents of all of which are incorporated herein by reference in their entirety.

FIELD OF THE INVENTION

The present invention relates to isoquinoline-5-carboxamide derivatives having an inhibitory activity against protein kinases, and a pharmaceutical composition comprising same as an active ingredient for the prevention and treatment of diseases associated with abnormal cell growth, which are caused by abnormal activation of protein kinases.

BACKGROUND OF THE INVENTION

A protein kinase plays a key role in mediation of signal transduction via phosphorylation of a hydroxyl group present in a tyrosine, serine or threonine residue of a protein, and, thus, is deeply involved in the regulation of cell growth, differentiation, proliferation, etc.

As is well known, a balance between the "on-state" and the "off-state" of an intracellular signaling pathway is essential for maintenance of homeostasis of a cell. When a normal intracellular signaling pathway is interrupted due to overexpression or mutation of a specific protein kinase (e.g., mostly continuation of the "on-state" of intracellular signals), it may cause various diseases such as cancer, inflammatory diseases, metabolic diseases and brain diseases. It is estimated that human genome contains 518 protein kinases which constitute approximately 1.7% of all human genes [Manning et al., *Science*, 298, (2002), 1912]; and the protein kinases can be divided into two major types: tyrosine protein kinases (90 species or more) and serine/threonine protein kinases. The tyrosine protein kinases can be divided into 58 species of receptor tyrosine kinases which can be further categorized into 20 subtypes, and 32 species of cytoplasmic/non-receptor tyrosine kinases which can be further categorized into 10 subtypes. A receptor tyrosine kinase has a kinase domain that can receive a growth factor on the surface of a cell, and an active site for phosphorylation of a tyrosine residue in cytoplasm. When a growth factor binds to the extracellular domain of the growth receptor, the receptor tyrosine kinase forms a polymer, which may result in autophosphorylation of specific tyrosine residues in the cytoplasmic active site. This may trigger a cascade of phosphorylation of downstream intracellular protein kinases that ultimately transmits the extracellular signal into the nucleus, thereby causing transcription of various genes and synthesis of various proteins that may be involved in cell growth, differentiation, proliferation and the like. In this process, it is known that if protein kinases are abnormally overexpressed or abnormally activated by mutation, this may induce various kinds of diseases such as cancer.

Among the various cytoplasmic kinases, Raf is one of the kinases that participate in mitogen-activated protein kinase (MAPK) pathway where a signal is initiated by the receptor protein kinase activated by a growth factor and transmitted via Ras-Raf-MEK (mitogen-activated protein kinase)-ERK (extracellular signal-regulated kinase) [Solit, D. B. et al., *Nature*, 439, (2006), 358]. Currently, it is known that Raf has three types of isoforms, i.e., A-Raf, B-Raf and C-Raf [Jansen H W, et al., *EMBO. J.*, 2, (1983), 1969; Marais R. et al., *Cancer Surv.*, 27, (1996), 101]. Since abnormal activation in the MAPK pathway has been observed in approximately 30% of human cancer tissues and gene mutation of B-Raf and C-Raf showing aberrant activation has been confirmed in cancer tissues, it is generally accepted that Raf plays a very important role in the MAPK pathway of cancer tissues.

Accordingly, there have been suggested methods of treating cancer by using a compound having an inhibitory effect against abnormal activities of Raf kinases. Hence, several Raf and modified Raf kinase inhibitors are being clinically used or currently under development for the treatment of cancer. Examples of such Raf kinase inhibitors include: sorafenib (Nexava®, Bayer) which is used for treatment of liver cancer, vemurafenib (PLX-4032, RG7204, Roche) which has been recently approved for treatment of melanoma, and drugs that are currently being tested in clinical trials such as regorafenib and RDEA119 by Bayer, RAF265 by Novartis, E3810 by Advan Chem, DCC2036 by Deciphera Pharma., CKI-27 by Chugai Pharma., RO-5126766 by Roche, and the like.

However, it is observed that many cancers develop a tolerance to said inhibitors. It has been postulated that the tolerance is caused by abnormal activation of MAPK pathway due to mutation of Raf, activation of complementary signaling system among different Raf isoforms, different signal transduction pathway depending on the subtypes (i.e., K-Ras, N-Ras and H-Ras) of Ras, which is a upstream protein of MAPK signal transduction, and, moreover, activation of signaling systems other than MAPK due to mutation of Ras.

In this connection, it has been proven that inhibition of Raf/MEK/ERK signaling system to suppress cell proliferation and inhibition of VEGFR2/PDGFR-β to suppress tumor angiogenesis may be effective against diseases caused by mutations in Raf and Ras [Allen, E. et al., *Clin. Cancer Res.*, 17, (2011), 5299].

SUMMARY OF THE INVENTION

Accordingly, it is an object of the present invention to provide a compound that is different from Raf inhibitors due to having an inhibitory activity against not only Raf but also other kinases such as VEGFR2/PDGFR-β, etc., which play an important role in signal transduction related to cell growth and differentiation.

It is another object of the present invention to provide a pharmaceutical composition comprising the compound as an active ingredient for the prevention and treatment of diseases associated with abnormal cell growth which are caused by abnormal activation of protein kinases.

In accordance with one aspect of the present invention, there is provided a compound selected from the group consisting of an isoquinoline-5-carboxamide derivative of formula (I), a pharmaceutically acceptable salt, an isomer, a hydrate and a solvate thereof:

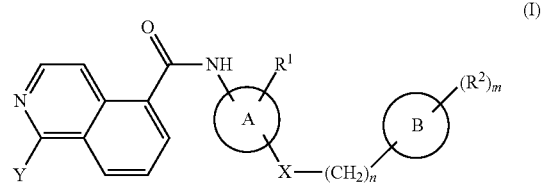

wherein,

A, B, X, Y, $R^1$, $R^2$, m and n are as defined in this specification.

In accordance with another aspect of the present invention, there is provided a pharmaceutical composition comprising the compound as an active ingredient for the prevention or treatment of diseases associated with abnormal cell growth, which are caused by abnormal activation of protein kinases.

The compound selected from the group consisting of an isoquinoline-5-carboxamide derivative, a pharmaceutically acceptable salt, an isomer, a hydrate and a solvate thereof in accordance with the present invention is effective for the prevention or treatment of diseases associated with abnormal cell growth, which are caused by abnormal activation of protein kinases.

DETAILED DESCRIPTION OF THE INVENTION

Hereinafter, the present invention is described in detail.

The term 'halogen' as used herein refers to a fluorine, chlorine, bromine or iodine, unless otherwise indicated.

The term 'alkyl' as used herein refers to a straight, cyclic or branched hydrocarbon residue, unless otherwise indicated.

The term 'cycloalkyl' as used herein refers to a cyclic alkyl including cyclopropyl, etc., unless otherwise indicated.

The term 'aryl' as used herein refers to an aromatic group including phenyl, naphthyl, etc., unless otherwise indicated.

The term 'heterocycloalkyl' as used herein refers to a cyclic alkyl, e.g., mono-, bi- or polycyclic alkyl, which contains at least one, for example, one to four heteroatoms, selected from O, N and S, unless otherwise indicated. Examples of mono-heterocycloalkyl include piperidinyl, morpholinyl, thiamorpholinyl, pyrrolidinyl, imidazolidinyl, tetrahydrofuranyl, piperazinyl and similar groups thereto, but are not limited thereto.

The term 'heteroaryl' as used herein refers to an aromatic group, e.g., mono-, bi- or polycyclic aromatic group, which contains heteroatoms selected from O, N and S. Examples of monocyclic heteroaryl include thiazolyl, oxazolyl, thiophenyl, furanyl, pyrrolyl, imidazolyl, isooxazolyl, pyrazolyl, triazolyl, thiadiazolyl, tetrazolyl, oxadiazolyl, pyridinyl, pyridazinyl, pyrimidinyl, pyrazinyl and similar groups thereto, but are not limited thereto. Examples of bicyclic heteroaryl include indolyl, benzothiophenyl, benzofuranyl, benzimidazolyl, benzoxazolyl, benzisoxazolyl, benzthiazolyl, benzthiadiazolyl, benztriazolyl, quinolinyl, isoquinolinyl, furinyl, furopyridinyl and similar groups thereto, but are not limited thereto.

The present invention provides a compound selected from the group consisting of an isoquinoline-5-carboxamide derivative of formula (I), a pharmaceutically acceptable salt, an isomer, a hydrate and a solvate thereof:

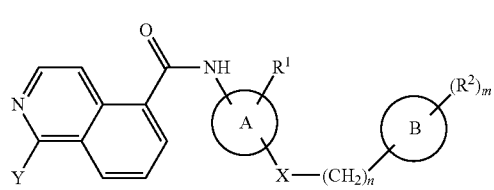

(I)

wherein,

A is $C_{6-10}$ aryl or $C_{5-10}$ heteroaryl;

B is $C_{1-6}$ alkyl, $C_{3-6}$ cycloalkyl, $C_{3-6}$ heterocycloalkyl, $C_{6-10}$ aryl or $C_{5-10}$ heteroaryl; X is —NH—, —C(O)NH—, —NHC(O)—, —NHC(O)NH—, —C(S)NH—, —NHC(S)—, —NHC(S)NH—, —NHSO$_2$— or —SO$_2$NH—;

Y is hydrogen, $C_{1-3}$ alkyl or $NR^3R^4$, wherein said $R^3$ and $R^4$ are each independently hydrogen, $C_{1-6}$ alkyl or —(CH$_2$)$_q$—Z—, wherein said Z is $NR^5R^6$, $C_{1-6}$ alkoxy, $C_{3-6}$ cycloalkyl, $C_{3-6}$ heterocycloalkyl, $C_{6-10}$ aryl or $C_{5-10}$ heteroaryl, wherein said $R^5$ and $R^6$ are each independently hydrogen, —NH$_2$, $C_{1-6}$ alkyl, $C_{1-6}$ alkoxy, $C_{3-6}$ cycloalkyl or $C_{3-6}$ heterocycloalkyl, said alkyl, alkoxy, cycloalkyl or heterocycloalkyl being unsubstituted or substituted with one or more halogen atoms, q is an integer ranging from 0 to 3;

$R^1$ is hydrogen, halogen, $C_{1-3}$ alkyl or $C_{1-3}$ alkoxy, wherein said alkyl or alkoxy is unsubstituted or substituted with one or more halogen atoms;

$R^2$ is hydrogen, halogen, —CF$_3$, —NO$_2$, —OH, $C_{1-6}$ alkoxy, $C_{1-6}$ alkyl, $C_{2-4}$ alkenyl, $C_{2-4}$ alkynyl, —NR$^7$R$^8$, —NHSO$_2$R$^9$, —SO$_2$R$^{10}$, —C(O)R$^{11}$, —NHC(O)R$^{12}$, —NHC(O)OR$^{13}$, $C_{3-6}$ cycloalkyl, $C_{3-6}$ heterocycloalkyl, $C_{6-10}$ aryl, $C_{6-10}$ aryloxy, $C_{5-10}$ heteroaryl or $C_{5-10}$ heteroaryloxy, wherein said $R^2$ is connected to B by —(CH$_2$)$_p$— or may be substituted with halogen, cyano, $C_{1-4}$ alkyl or $C_{1-4}$ alkylcarbonyl, wherein said $R^7$, $R^8$, $R^9$, $R^{10}$, $R^{11}$, $R^{12}$ and $R^{13}$ are each independently hydrogen, —NH$_2$, $C_{1-6}$ alkyl, $C_{1-6}$ alkoxy, $C_{3-6}$ cycloalkyl or $C_{3-6}$ heterocycloalkyl, said alkyl, alkoxy, cycloalkyl or heterocycloalkyl being unsubstituted or substituted with one or more halogen atoms, and p is 1 or 2;

m is an integer ranging from 0 to 5; and n is an integer ranging from 0 to 2.

The compound of the present invention may also form a pharmaceutically acceptable salt. Such salt may be a pharmaceutically acceptable non-toxic acid addition salt containing anion, but not limited thereto. For example, the salt may include acid addition salts formed by inorganic acids such as hydrochloric acid, sulfuric acid, nitric acid, phosphoric acid, hydrobromic acid, hydroiodic acid and others; organic carbonic acids such as tartaric acid, formic acid, citric acid, acetic acid, trichloroacetic acid, trifluoroacetic acid, gluconic acid, benzoic acid, lactic acid, fumaric acid, maleic acid and others; and sulfonic acids such as methanesulfonic acid, benzenesulfonic acid, p-toluenesulfonic acid, naphthalensulfonic acid and others. Among them, acid addition salts formed by sulfuric acid, methanesulfonic acid or hydrohalogenic acid and others are preferred.

Further, the compound of the present invention can have an asymmetric carbon center, and thus may be present in the form of R or S isomers, racemic compounds, diastereomeric mixtures, or individual diastereomers, such entire isomers and mixtures being included within the scope of the present invention.

In addition, solvates and hydrates of the compound of formula (I) are encompassed within the scope of the present invention.

In one embodiment of the isoquinoline-5-carboxamide derivative of formula (I) of the present invention, A is phenyl or isoquinoline.

In another embodiment of the isoquinoline-5-carboxamide derivative of formula (I) of the present invention, B is aryl or heteroaryl.

In another embodiment of the isoquinoline-5-carboxamide derivative of formula (I) of the present invention, X is —NH—, —C(O)NH—, —NHC(O)— or —NHC(O)NH—.

In another embodiment of the isoquinoline-5-carboxamide derivative of formula (I) of the present invention, Y is hydrogen, amino, —NHCH(CH$_3$)$_3$, or

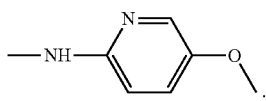

In another embodiment of the isoquinoline-5-carboxamide derivative of formula (I) of the present invention, A is phenyl or isoquinoline; B is aryl or heteroaryl; X is —NH—, —C(O)NH—, —NHC(O)— or —NHC(O)NH—; and Y is hydrogen, amino, —NHCH(CH$_3$)$_3$, or

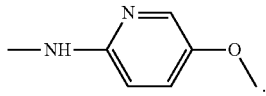

The preferred examples of the isoquinoline-5-carboxamide derivative of formula (I) of the present invention are further exemplified below. In addition to the derivatives, pharmaceutically acceptable salts, isomers, hydrates or solvates thereof may also be included in the present invention:

1) 1-amino-N-(2-methyl-5-(3-(trifluoromethyl)benzamido)phenyl)isoquinoline-5-carboxamide;
2) 1-(t-butylamino)-N-(2-methyl-5-((3-(trifluoromethyl)phenyl)carbamoyl)phenyl)isoquinoline-5-carboxamide;
3) 1-amino-N-(2-methyl-5-((3-(trifluoromethyl)phenyl)carbamoyl)phenyl)isoquinoline-5-carboxamide;
4) 1-amino-N-(5-((4-chloro-3-(trifluoromethyl)phenyl)carbamoyl)-2-methylphenyl)isoquinoline-5-carboxamide;
5) 1-amino-N-(5-((3-(2-cyanopropan-2-yl)phenyl)carbamoyl)-2-methylphenyl)isoquinoline-5-carboxamide;
6) 1-(t-butylamino)-N-(5-((4-((4-ethylpiperazin-1-yl)methyl)-3-(trifluoromethyl)phenyl)carbamoyl)-2-methylphenyl)isoquinoline-5-carboxamide;
7) 1-amino-N-(5-((4-((4-ethylpiperazin-1-yl)methyl)-3-(trifluoromethyl)phenyl)carbamoyl)-2-methylphenyl)isoquinoline-5-carboxamide;
8) 1-(t-butylamino)-N-(2-methyl-5-(phenylcarbamoyl)phenyl)isoquinoline-5-carboxamide;
9) 1-amino-N-(2-methyl-5-((4-(trifluoromethyl)pyridin-2-yl)carbamoyl)phenyl)isoquinoline-5-carboxamide;
10) 1-amino-N-(5-((4,6-dimethylpyridin-2-yl)carbamoyl)-2-methylphenyl)isoquinoline-5-carboxamide;
11) 1-amino-N-(2-methyl-5-((3-(4-methyl-1H-imidazol-1-yl)-5-(trifluoromethyl)phenyl)carbamoyl)phenyl)isoquinoline-5-carboxamide;
12) 1-(t-butylamino)-N-(5-(3-(4-chloro-3-(trifluoromethyl)phenyl)ureido)-2-methylphenyl)isoquinoline-5-carboxamide;
13) 1-amino-N-(5-(3-(4-chloro-3-(trifluoromethyl)phenyl)ureido)-2-methylphenyl)isoquinoline-5-carboxamide;
14) 1-amino-N-(2-methyl-5-(3-(3-(trifluoromethyl)phenyl)ureido)phenyl)isoquinoline-5-carboxamide;
15) 1-(t-butylamino)-N-(5-(3-(2-fluoro-5-(trifluoromethyl)phenyl)ureido)-2-methylphenyl)isoquinoline-5-carboxamide;
16) 1-amino-N-(5-(3-(2-fluoro-5-(trifluoromethyl)phenyl)ureido)-2-methylphenyl)isoquinoline-5-carboxamide;
17) 1-amino-N-(3-((3-(trifluoromethyl)phenyl)carbamoyl)phenyl)isoquinoline-5-carboxamide;
18) 1-amino-N-(6-methyl-1-((3-(trifluoromethyl)phenyl)amino)isoquinolin-5-yl)isoquinoline-5-carboxamide;
19) 1-((5-methoxypyridin-2-yl)amino)-N-(2-methyl-5-(3-(trifluoromethyl)benzamido)phenyl)isoquinoline-5-carboxamide;
20) 1-((5-methoxypyridin-2-yl)amino)-N-(2-methyl-5-(3-(3-(trifluoromethyl)phenyl)ureido)phenyl)isoquinoline-5-carboxamide;
21) 1-((5-methoxypyridin-2-yl)amino)-N-(2-methyl-5-((3-(trifluoromethyl)phenyl)carbamoyl)phenyl)isoquinoline-5-carboxamide;
22) N-(2-methyl-5-(3-(trifluoromethyl)benzamido)phenyl)isoquinoline-5-carboxamide; and
23) N-(1-((4-chlorophenyl)amino)-6-methylisoquinolin-5-yl)isoquinoline-5-carboxamide.

Hereinafter, an exemplary method for preparing the compound in accordance with the present invention is explained.

The following abbreviations are used in Preparation Examples, Preparation Methods and Examples:

DECP: diethyl chlorophosphate
DIPEA: N,N-diisopropylethylamine
HATU: [2-(1H-9-azabenzotriazol-1-yl)-1,1,3,3-tetramethyluronium hexafluorophosphate]
HOBT: N-hydroxybenzotriazole
DMF: N,N-dimethyl formamide
DMSO: dimethyl sulfoxide EA: ethyl acetate
CH$_2$Cl$_2$: dichloromethane EtOAc: ethylacetate
Na$_2$SO$_4$: anhydrous sodium sulfate NaOH: sodium hydroxide
Zn(CN)$_2$: zinc cyanide THF: tetrahydrofuran
Cs$_2$CO$_3$: cesium carbonate AIBN: azobisisobutyronitrile
Pd$_2$(dba)$_3$: tris(dibenzylideneacetone)dipalladium(0)

The compound of formula (I) in accordance with the present invention may be prepared via Reaction Schemes 3 and 4 by using intermediates obtained in Reaction Schemes 1 and 2 below or commercially available intermediates.

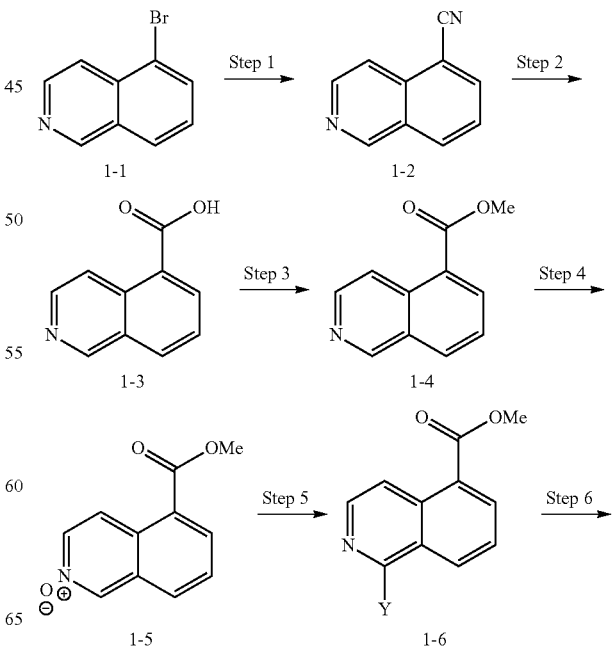

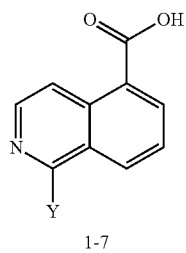

Reaction Scheme 1 may be used in the manufacture of the compound of formula (I), and the compounds of formula (I) wherein Y is —$NH_2$ may be prepared from the compounds of formula (1-7) wherein Y is —NH(tBu).

The above reaction processes are explained stepwise below.

<Step 1>

5-Bromoisoquinoline (compound (1-1), 1.0 eq., standard equivalent unit) and dimethyl formamide (2.5~2.8 L/mol, based on the standard equivalent unit) are mixed and stirred. The reaction solution is added with $Zn(CN)_2$ (0.6~0.7 eq.) and $Ph(PPH)_4$ (0.04~0.05 eq.), and stirred for about 3.5~4.5 hours at 90~110° C. The reaction mixture is cooled to room temperature, diluted with ethyl acetate, and washed with a saturated aqueous sodium bicarbonate and saline. The organic layer thus obtained is dried over anhydrous sodium sulfate, filtered and concentrated under reduced pressure to obtain the compound (1-2).

<Step 2>

The compound (1-2) (1.0 eq., standard equivalent unit) and distilled water (2.8~3.3 L/mol, based on the standard equivalent unit) are mixed and stirred. The reaction solution is added with concentrated HCl (0.3~0.5 L/mol, based on the standard equivalent unit), and stirred for about 4~7 hours at 90~110° C. The reaction mixture is cooled to room temperature and added with DIPEA (1.0~1.2 L/mol, based on the standard equivalent unit) to adjust a pH value to a range of 5~6. The resulting solid mixture is stirred for about 2.5~3.5 hours at room temperature and filtered. The residue thus obtained is dried in an oven at 45~55° C. to obtain the compound of formula (1-3).

<Step 3>

The compound (1-3) (1.0 eq., standard equivalent unit) and methanol (3.0~4.0 L/mol, based on the standard equivalent unit) are mixed and stirred. The reaction solution is slowly added with sulfuric acid (7.5~8.5 eq.) and refluxed for about 18~22 hours. The reaction mixture is cooled to room temperature, and the solvent is distilled under reduced pressure. The concentrate thus obtained is added with distilled water, and adjusted to have a pH value in a range of 10~11 by adding DIPEA. The resulting solution is diluted with ethyl acetate, and washed with a saturated aqueous sodium bicarbonate and saline. The organic layer thus obtained is dried over anhydrous sodium sulfate, filtered and concentrated under reduced pressure to obtain the compound (1-4).

<Step 4>

The compound (1-4) (1.0 eq., standard equivalent unit) and dichloromethane (2.0~2.5 L/mol, based on the standard equivalent unit) are mixed and stirred. The reaction solution is added with mCPBA (1.4~1.6 eq.), and stirred for about 4.5~5.5 hours at 45~55° C. The reaction mixture is cooled down to room temperature, and adjusted to have a pH value in a range of 9~10 by added with saturated aqueous sodium bicarbonate. The resulting solution is diluted with dichloromethane, and washed with a saturated aqueous sodium bicarbonate and saline. The organic layer thus obtained is dried over anhydrous sodium sulfate, filtered and concentrated under reduced pressure to obtain the compound (1-5).

<Step 5>

The compound (1-5) (1.0 eq., standard equivalent unit) and trifluorotoluene (9.0~12.0 L/mol, based on the standard equivalent unit) are mixed and stirred. The reaction solution is slowly added with an amine (3.0~5.0 eq.), which corresponds to Y of the compound of formula (I), and p-toluenesulfonic acid anhydride (1.9~2.1 eq.) at about 0~7° C., and then stirred for about 1.5~2.5 hours at the same temperature (0~7° C.). The reaction mixture is diluted with ethyl acetate, and washed with a saturated aqueous sodium bicarbonate and saline. The organic layer thus obtained is dried over anhydrous sodium sulfate, filtered and concentrated under reduced pressure to obtain the compound (1-6).

<Step 6>

The compound (1-6) (1.0 eq., standard equivalent unit) is stirred in tetrahydrofuran (2.0~3.5 L/mol, based on the standard equivalent unit) and distilled water (2.0~3.5 L/mol, based on the standard equivalent unit). The reaction solution is added with LiOH (2.0α2.5 eq.), and stirred for about 11~13 hours at 70α90° C. The reaction mixture is cooled to room temperature, and adjusted to have a pH value in a range of 1α2 by adding 1N aqueous HCl solution. The reaction mixture is diluted with ethyl acetate, and washed with distilled water. The organic layer thus obtained is dried over anhydrous sodium sulfate, filtered and concentrated under reduced pressure to obtain the compound (1-7).

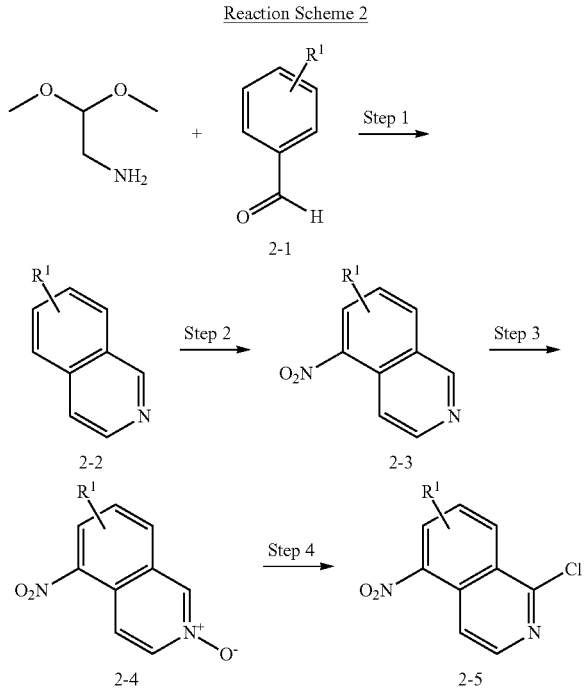

Reaction Scheme 2 illustrates a reaction process when A in the compound of formula (I) is isoquinoline, wherein $R^1$ is as defined in formula (I). The reaction process is explained stepwise below.

<Step 1>

Benzaldehyde substituted with $R^1$ (compound (2-1), 1.0 eq., standard equivalent unit) and chloroform (1.6~2.0 L/mol, based on the standard equivalent unit) are mixed and stirred, which is then slowly added with aminoacetaldehyde dimethyl acetal (1.0~1.2 eq.), followed by stirring at 80~95° C. until about a half of the reaction solution evaporates. The reaction solution is cooled to room temperature, and the resulting yellow reaction solution is dissolved in chloroform (0.8~1.0 L/mol, based on the standard equivalent unit) and then cooled to 0~5° C. or below. The reaction solution is slowly added with ethyl chloroformate (1.0~1.2 eq.) and triethyl phosphite (1.2~1.4 eq.) over 0.5~1.0 hour and then stirred for 20~28 hours at room temperature. The reaction solution is cooled to 0~5° C. or below, slowly added with titanium tetrachloride (3.8~4.2 eq.) over 0.5~1.0 hour, and refluxed for 10~14 hour or more. The reaction solution is cooled to room temperature and stirred for 10~14 hours or more. The reaction mixture is poured over an ice water to separate the organic layer and the aqueous layer, and the aqueous layer is washed with dichloromethane. The aqueous layer is poured into a saturated potassium sodium tartrate solution, adjusted to have a pH value in a range of 8.0~9.5 by adding an aqueous ammonia solution, and then extracted with $CH_2Cl_2$. The organic layer thus obtained is dried over anhydrous sodium sulfate and concentrated under reduced pressure to obtain the compound (2-2).

<Step 2>

The compound (2-2) (1.0 eq., standard equivalent unit) is mixed with sulfuric acid (approximately 8~12 vol., based on the standard equivalent unit) and stirred. The reaction solution is cooled to 0~5° C. or below, slowly added with potassium nitrate (2.0~2.2 eq.), and stirred for 3~4 hours or more at 0~5° C. The reaction mixture is poured over an ice water, adjusted to have a pH value in a range of 11~12 by adding 5N aqueous NaOH solution, and stirred for 11~13 hours or more at room temperature. The resulting solid is filtered under reduced pressure, and the filtered solid is washed with water. The filtered solid is dried with warm wind in an oven (35~45° C.) for 3~4 hours or more to obtain the compound (2-3).

<Step 3>

The compound (2-3) (1.0 eq., standard equivalent unit) is dissolved in $CH_2Cl_2$ (2.8~3.3 L/mol, based on the standard equivalent unit), and the reaction solution is cooled to a temperature of 0~5° C. or below. The reaction solution is slowly added with mCPBA (1.5~1.7 eq.) over 0.5~1 hour, and stirred for 10~11 hours or more at 0~5° C. The reaction mixture is adjusted to have a pH value in a range of 10~11 by adding 1N aqueous NaOH solution, and extracted with $CH_2Cl_2$. The combined organic layer is dried over anhydrous sodium sulfate and concentrated under reduced pressure to obtain the compound (2-4).

<Step 4>

The compound (2-4) (1.0 eq., standard equivalent unit) is dissolved in 1,2-dichloroethane (8~9 L/mol, based on the standard equivalent unit), added with $POCl_3$ (4.5~5.5 eq.), and refluxed for 6~7 hours. The reaction solution is cooled to room temperature and concentrated by distilling the solvent under reduced pressure. The concentrated solid is dissolved in dichloromethane, added with an ice water, and the mixed solution thus obtained is subjected to extraction with dichloromethane. The combined organic layer is dried over anhydrous sodium sulfate and concentrated under reduced pressure. A mixed solution of ethyl acetate/hexane=1/1 (v/v) is added to the concentrated solid, followed by stirring for 2.0~2.5 hours or more at room temperature. The resulting solid is filtered under reduced pressure, and washed with a mixed solution of ethyl acetate/hexane=1/1 (v/v). The filtered solid is dried with warm wind in an oven (35~45° C.) for 3~4 hours or more to obtain the compound (2~5).

Reaction Scheme 3 illustrates a reaction process for the preparation of the compound of formula (I) when X=—NHC(O)—, and Reaction Scheme 4 illustrates a reaction process for the preparation of the compound of formula (I) when X=—C(O)NH—. Reaction processes for the preparation of the compound of formula (I) wherein X is —NH— or —NHC(O)NH— are described in detail in Examples below.

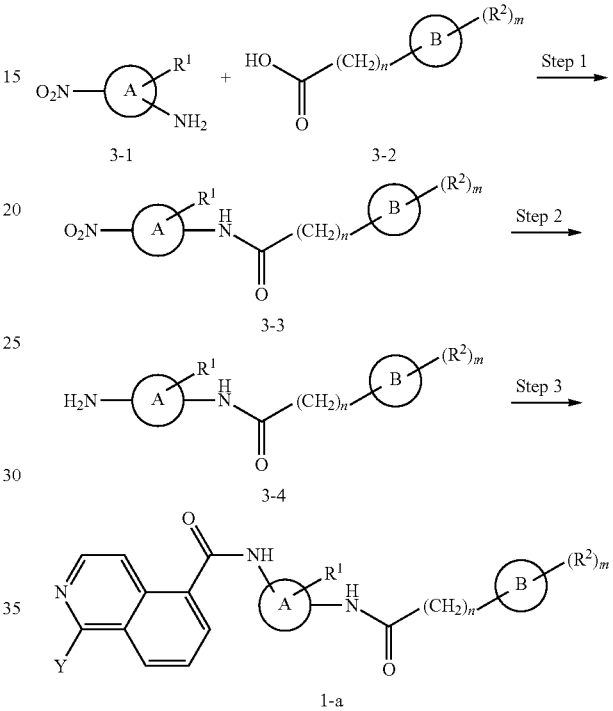

Reaction Scheme 3

Reaction Scheme 3 illustrates a reaction process for the preparation of the compound of formula (I), i.e. compound (1-a) when X=—NHC(O)— wherein A, B, Y, $R^1$, $R^2$, m and n are as defined in formula (I). Also, the compound of formula (I) wherein Y is $NH_2$ may be prepared from the compound of formula (1-a) wherein Y is NH(tBu).

<Step 1>

The compound (3-1) (1.0 eq., standard equivalent unit) is stirred in a solvent of dichloromethane (3.0~4.0 L/mol, based on the standard equivalent unit). The reaction solution is added with DIPEA (1.9~2.4 eq.) and the compound (3~2) (1.0~1.1 eq.), followed by stirring for about 1.0~1.5 hours at room temperature. The reaction mixture is washed with 1M aqueous HCl solution, an aqueous sodium bicarbonate solution and saline. The organic layer thus obtained is dried over anhydrous sodium sulfate, filtered and concentrated under reduced pressure to obtain the compound (3-3).

<Step 2>

The compound (3-3) (1.0 eq., standard equivalent unit) is stirred in a solvent of methanol (0.8~2.0 L/mol, based on the standard equivalent unit). The reaction solution is mixed with Pd/C (0.25~0.35 eq.), followed by stirring under hydrogen conditions for about 1.5~2.5 hours at room temperature. The reaction mixture is filtered through a Celite pad under reduced pressure, and washed with methanol. The filtrate is concentrated under reduced pressure to obtain the compound (3-4).

<Step 3>

The compound (1-7) obtained in Step 6 of Reaction Scheme 1 (1.0 eq., standard equivalent unit) is dissolved in a solvent of dimethyl formamide (2.0~3.5 L/mol, based on the standard equivalent unit), added with HATU (1.0~2.0 eq.) and DIPEA (2.0~4.0 eq.), followed by stirring for 8~20 minutes. The reaction mixture is added with the compound (3-4) (1.0~1.2 eq.), and stirred for 11~13 hours or more at room temperature. The reaction mixture is diluted with ethyl acetate, and washed with a saturated sodium bicarbonate solution and saline. The resulting organic layer is dried over anhydrous sodium sulfate, filtered and concentrated under reduced pressure. The concentrated compound is purified using silica gel chromatography to obtain the compound of formula (1-a).

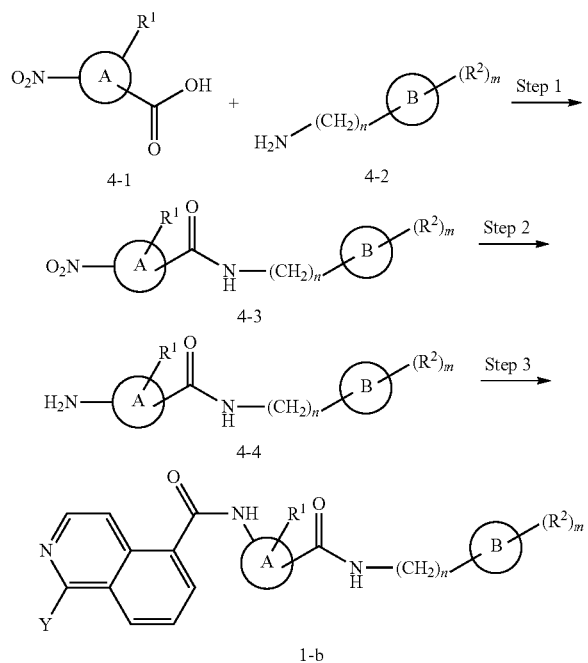

Reaction Scheme 4

Reaction Scheme 4 illustrates a reaction process for the preparation of the compound of formula (I), i.e., compound (1-b) when X=—C(O)NH— wherein A, B, Y, $R^1$, $R^2$, m and n are as defined in formula (I). Also, the compound of formula (I) wherein Y is $NH_2$ may be prepared from the compound of formula (1-b) wherein Y is NH(tBu). The above reaction processes are explained stepwise below.

<Step 1>

The compound (4-1) (1.0 eq., standard equivalent unit, 14.6 g, 81.0 mmol) is stirred in a solution of dimethyl formamide (1.8~2.6 L/mol, based on the standard equivalent unit). The reaction solution is added with HATU (1.2~1.8 eq.), DIPEA (1.4~2.2 eq.) and the compound (4-2) (1.2~1.8 eq.), followed by stirring for about 11~13 hours at room temperature. The reaction mixture is diluted with ethyl acetate, and washed with a saturated aqueous sodium bicarbonate solution and saline. The resulting organic layer is dried over anhydrous sodium sulfate, filtered and concentrated under reduced pressure. The concentrated solid is added with ethyl acetate, followed by stirring for 1.5~2.5 hours or more. The resulting solid is filtered under reduced pressure, and washed with ethyl acetate and methanol. The filtered solid is dried with warm wind in an oven (35~45° C.) for 2~4 hours or more to obtain the compound (4-3).

<Step 2>

The compound (4-3) (1.0 eq., standard equivalent unit) is stirred in a solvent of methanol (0.8~2.0 L/mol, based on the standard equivalent unit). The reaction solution is mixed with Pd/C (0.25~0.35 eq.), followed by stirring under hydrogen conditions for about 1.5~2.5 at room temperature. The reaction mixture is filtered through a Celite pad under reduced pressure, and washed with methanol. The filtrate is concentrated under reduced pressure to obtain the compound (4-4).

<Step 3>

The compound (1-7) obtained in Step 6 of Reaction Scheme 1 (1.0 eq., standard equivalent unit) is dissolved in dimethyl formamide (2.0~3.5 L/mol, based on the standard equivalent unit), added with HATU (1.0~2.0 eq.) and DIPEA (2.0~4.0 eq.), and stirred for 8~20 minutes. The reaction mixture is added with the compound (4-4) (1.0~1.2 eq.), followed by stirring for 11~13 hours or more at room temperature. The reaction mixture is diluted with ethyl acetate, and washed with a saturated aqueous sodium bicarbonate and saline. The organic layer thus obtained is dried over anhydrous sodium sulfate, filtered and concentrated under reduced pressure. The concentrated compound is purified using silica gel chromatography to obtain the compound (4-5).

The synthesis of derivatives of the present invention may be performed by employing a general reaction scheme such as Reaction Schemes 1, 2, 3 and 4 shown above.

Further, the present invention provides a pharmaceutical composition for the prevention and treatment of diseases associated with abnormal cell growth, which are caused by abnormal activation of protein kinases, comprising a compound selected from the group consisting of an isoquinoline-5-carboxamide derivative of formula (I), a pharmaceutically acceptable salt, an isomer, a hydrate and a solvate thereof as an active ingredient.

The protein kinase may be selected from the group consisting of A-RAF, B-RAF, C-RAF, PDGFR alpha, PDGFR beta, VEGRF and a combination thereof, against with pharmaceutical composition in accordance with the present invention has good inhibitory activity.

The diseases associated with the abnormal cell growth diseases for which the inventive pharmaceutical composition is effective may be selected from the group consisting of gastric cancer, lung cancer, liver cancer, colorectal cancer, small intestine cancer, pancreatic cancer, brain cancer, bone cancer, melanoma, breast cancer, sclerosing adenosis, uterine cancer, cervical cancer, head and neck cancer, esophagus cancer, thyroid cancer, parathyroid cancer, renal cancer, sarcoma, prostate cancer, urethral cancer, bladder cancer, leukemia, multiple myeloma, blood cancer, lymphoma, fibroadenoma, inflammation, diabetes, obesity, psoriasis, rheumatoid arthritis, hemangioma, acute or chronic kidney disease, coronary restenosis, autoimmune diseases, asthma, neurodegenerative diseases, acute infection and ocular diseases caused by angiogenesis.

The inventive pharmaceutical composition may be formulated in accordance with conventional methods, and may be prepared in the form of oral formulations such as a tablet, a pill, powders, a capsule, syrup, an emulsion, a microemulsion and others or parenteral formulations e.g., for intramuscular, intravenous or subcutaneous administration.

For oral formulations, carriers such as cellulose, calcium silicate, corn starch, lactose, sucrose, dextrose, calcium phosphate, stearic acid, magnesium stearate, calcium stearate, gelatin, talc, surfactants, suspending agents, emulsifying agents, diluting agents and others may be used. For injectable formulations, carriers such as water, saline, glucose solution, glucose solution analogs, alcohols, glycols, ethers (e.g., polyethylene glycol 400), oils, fatty acids, fatty acid esters, glycerides, surfactants, suspending agents, emulsifying agents and other may be used.

The administration dose of the active ingredient, i.e., the inventive compound of formula (I) or a pharmaceutically acceptable salt thereof, will be dependent on a variety of factors, including the age, weight, sex, health condition, degree of disease of the subject being treated, the severity of the affliction, the manner of administration, and the judgment of the prescribing physician. For example, the compound of formula (I) may be administered to a mammal including a human being orally or parenterally in a range of 0.01 to 200 mg/kg (body weight), preferably 10 to 100 mg/kg (body weight), once or twice a day or in accordance with an on/off schedule. In some cases, a recommended dosage may be less than said range or more than said range, as long as it would not cause adverse side effects. When a large amount of the inventive compound is administered, it may be administered in divided doses per day.

Further, the present invention provides a compound library comprising one or more selected from the group consisting of the inventive compound, a pharmaceutically acceptable salt thereof, an isomer, a hydrate and a solvate thereof.

Also, the present invention provides a method for the prevention and treatment of the diseases associated with abnormal cell growth, which are caused by abnormal activation of protein kinases, which comprises administering to the subject in need thereof the compound of formula (I) of the present invention. Furthermore, the present invention provides a use of the compound of formula (I) for the prevention or treatment of the diseases associated with abnormal cell growth, which are caused by abnormal activation of protein kinases.

Hereinafter, the present invention is described more specifically by the following Examples, but these are provided only for illustration purposes, and the present invention is not limited thereto.

Preparation Example 1

Preparation of 1-aminoisoquinoline-5-carboxylic acid

Step (1): Preparation of isoquinoline-5-carbonitrile

5-Bromoisoquinoline (8 g, 38.65 mmol) and dimethyl formamide (100 mL) were mixed and stirred. The reaction solution was added with $Zn(CN)_2$ (2.72 g, 23.19 mmol) and $Ph(PPH)_4$ (1.78 g, 1.55 mmol), followed by stirring for about 4 hours at 100° C. The reaction mixture was cooled to room temperature, diluted with ethyl acetate, and washed with a saturated aqueous sodium bicarbonate solution and saline. The resulting organic layer was dried over anhydrous sodium sulfate, filtered and concentrated under reduced pressure to obtain the title compound (5.8 g, 97%).

$^1$H-NMR Spectrum (300 MHz, DMSO-$d_6$): δ 9.45 (s, 1H), 8.72 (d, 1H), 8.50 (d, 1H), 8.39 (d, 1H), 7.94 (d, 1H), 7.85 (t, 1H).

MS (ESI$^+$, m/z): 155 [M+H]$^+$

Step (2): Preparation of isoquinoline-5-carboxylic acid

Isoquinoline-5-carbonitrile (6 g, 38.62 mmol) obtained in Step (1) above and distilled water (90 mL) were mixed and stirred. The reaction solution was added with concentrated HCl solution (15 mL) and stirred for about 6 hours at 100° C. The reaction mixture was cooled to room temperature and adjusted to have a pH value in a range of 5~6 by adding DIPEA (about 40 mL). The resulting solid mixture was stirred for about 3 hours at room temperature and filtered. The residue was dried in an oven at 50° C. to obtain the title compound (5.6 g, 84%).

MS (ESI$^+$, m/z): 174 [M+H]$^+$

Step (3): Preparation of methyl isoquinoline-5-carboxylate

Isoquinoline-5-carboxylic acid (5.6 g, 32.36 mmol) obtained in Step (2) above and methanol (90 mL) were mixed and stirred. The reaction solution was slowly added with sulfuric acid (15 mL, 259 mmol) and refluxed for about 20 hours. The reaction mixture was cooled to room temperature, and the solvent was distilled under reduced pressure. The concentrate was added with distilled water and adjusted to have a pH value in a range of 10~11 by adding DIPEA. The reaction mixture was diluted with ethyl acetate, and washed with a saturated aqueous sodium bicarbonate solution and saline. The organic layer thus obtained was dried over anhydrous sodium sulfate, filtered, and concentrated under reduced pressure to obtain the title compound (5.8 g, 96%).

$^1$H-NMR Spectrum (300 MHz, DMSO-$d_6$): δ 9.47 (s, 1H), 8.73 (m, 2H), 8.45 (m, 2H), 7.81 (t, 1H), 3.97 (s, 3H).

MS (ESI$^+$, m/z): 188 [M+H]$^+$

Step (4): Preparation of 5-(methoxycarbonyl)isoquinoline 2-oxide

Methyl isoquinoline-5-carboxylate (5.8 g, 31.0 mmol) obtained in Step (3) above and dichloromethane (60 mL) were mixed and stirred. The reaction solution was added with mCPBA (8.02 g, 46.2 mmol) and stirred for about 5 hours at 50° C. The reaction mixture was cooled to room temperature and adjusted to have a pH value in a range of 9~10 by adding a saturated aqueous sodium bicarbonate. The reaction mixture was diluted with dichloromethane, and washed with a saturated aqueous sodium bicarbonate solution and saline. The organic layer thus obtained was dried over anhydrous sulfate, filtered, and concentrated under reduced pressure to obtain the title compound (4 g, 63.5%).

$^1$H NMR Spectrum (300 MHz, DMSO-$d_6$): δ 9.05 (s, 1H), 8.68 (d, 1H), 8.28 (d, 1H), 8.14 (d, 1H), 7.78 (t, 1H), 3.93 (s, 3H).

MS (ESI$^+$, m/z): 204 [M+H]$^+$

Step (5): Preparation of methyl 1-(t-butylamino)isoquinoline-5-carboxylate 5-(Methoxycarbonyl)isoquinoline 2-oxide (2.0 g, 9.84 mmol) obtained in Step (4) above and trifluorotoluene (20 mL) were mixed and stirred. The reaction solution was slowly added with t-butylamine (3.6 g, 49.25 mmol) and p-toluenesulfonic acid anhydride (6.42 g, 19.68 mmol) at about 5° C., and stirred for about 2 hours at the same temperature (~5° C.). The reaction mixture was diluted with ethyl acetate, and washed with a saturated aqueous sodium bicarbonate solution and saline. The organic layer thus obtained was dried over anhydrous sodium sulfate, filtered, and concentrated under reduced pressure to obtain the title compound (1.6 g, 64%).

$^1$H-NMR Spectrum (300 MHz, DMSO-$d_6$): δ 8.57 (d, 1H), 8.20 (d, 1H), 7.98 (d, 1H), 7.66 (d, 1H), 7.55 (t, 1H), 6.66 (s, 1H), 3.90 (s, 3H), 1.52 (s, 9H).

MS (ESI$^+$, m/z): 259 [M+H]$^+$

Step (6): Preparation of 1-(t-butylamino)isoquinoline-5-carboxylic acid

Methyl 1-(t-butylamino)isoquinoline-5-carboxylate (1.6 g, 6.20 mmol) obtained in Step (5) above was stirred in a solution of tetrahydrofuran (16 mL) and distilled water (16 mL). The reaction solution was added with LiOH (0.57 g, 13.6 mmol) and stirred for about 12 hours at 80° C. The reaction mixture was cooled to room temperature and adjusted to have a pH value in a range of 1~2 by adding 1N aqueous HCl. The reaction mixture was diluted with ethyl acetate, and washed with distilled water. The organic layer thus obtained was dried over anhydrous sodium sulfate, filtered, and concentrated under reduced pressure to obtain the title compound (0.6 g, 40%).

$^1$H-NMR Spectrum (300 MHz, CDCl$_3$): δ 11.7 (s, 1H), 8.52 (d, 1H), 8.20 (d, 1H), 7.95 (d, 1H), 7.77 (d, 1H), 7.52 (t, 1H), 6.61 (s, 1H), 1.52 (s, 9H).

MS (ESI$^+$, m/z): 245 [M+H]$^+$

Step (7): Preparation of 1-aminoisoquinoline-5-carboxylic acid hydrochloride 1-(t-Butylamino)isoquinoline-5-carboxylic acid (35 mg, 0.28 mmol) obtained in Step (6) above was stirred in a solvent of distilled water (0.4 mL). The reaction solution was added with concentrated HCl (0.15 mL), followed by stirring for about 3 hours at 90° C. The reaction mixture was cooled to room temperature, and the solvent was distilled under reduced pressure. The concentrate was added with toluene, followed by distillation under reduced pressure for 2~3 times to obtain the title compound (30 mg, 66%).

MS (ESI$^+$, m/z): 189 [M+H]$^+$

Preparation Example 2

Preparation 1-Chloro-6-Methyl-5-Nitroisoquinoline

Step (1): Preparation of 6-methylisoquinoline p-Tolualdehyde (53 mL, 0.486 mol) was stirred in a solvent of chloroform (900 mL), slowly added with aminoacetaldehyde dimethyl acetal (59.3 mL, 0.486 mol), and stirred at 90° C. until about a half of the reaction solution had evaporated. The reaction solution was cooled to room temperature, and the yellow reaction solution was dissolved in chloroform (400 mL), followed by cooling to 0° C. or lower. The reaction solution was slowly added with ethyl chloroformate (48 mL, 0.486 mol) and triethyl phosphite (104 mL, 0.583 mol), followed by stirring for 24 hours at room temperature. The reaction solution was cooled to 0° C. or lower, slowly added with titanium tetrachloride (213.6 mL, 1.94 mol), and refluxed for 12 hours or more. The temperature of the reaction solution was adjusted to room temperature and stirred for over 12 hours. The reaction mixture was poured over an ice water to separate the organic layer and the aqueous layer, and the aqueous layer was washed with dichloromethane. The aqueous layer was poured into a saturated potassium sodium tartrate solution, and adjusted to have a pH value of 9 by adding an aqueous ammonia solution, and then extracted with dichloromethane. The combined organic layer thus obtained was dried over anhydrous sodium sulfate and concentrated under reduced pressure to obtain the title compound (46.3 g, 66%).

$^1$H-NMR Spectrum (300 MHz, DMSO-d$_6$): δ 9.23 (s, 1H), 8.45 (d, 1H), 8.02 (d, 1H), 7.72 (d, 2H), 7.54 (d, 1H), 2.49 (s, 3H)

Step (2): Preparation of 6-methyl-5-nitroisoquinoline

6-Methylisoquinoline (46.3 g, 0.323 mol) obtained in Step (1) was mixed with sulfuric acid (400 mL) and stirred. The temperature of the reaction solution was cooled to 0° C. or lower, slowly added with potassium nitrate (65.3 g, 0.646 mol) and stirred for 3 hours or more at 0° C. The reaction mixture was added with an ice water, and adjusted to have a pH value of 12 by adding 5N aqueous NaOH solution, followed by stirring for 12 hours or more at room temperature. The solid thus obtained was filtered under reduced pressure, and the resulting solid was washed with water. The filtered solid was dried with warm wind in an oven (40° C.) for 3 hours or more to obtain the title compound (43.3 g, 71%).

$^1$H NMR Spectrum (300 MHz, DMSO-d$_6$): δ 9.46 (s, 1H), 8.67 (d, 1H), 8.37 (d, 1H), 7.79 (d, 1H), 7.62 (d, 1H), 2.54 (s, 3H)

Step (3): Preparation of 6-methyl-5-nitroisoquinoline-2-oxide

6-Methyl-5-nitroisoquinoline (43.3 g, 0.230 mol) obtained in Step (2) above was dissolved in dichloromethane (650 mL), and the temperature of the reaction solution was cooled to 0° C. or lower. The reaction solution was slowly added with mCPBA (67.5 g, 0.390 mol), followed by stirring for 10 hours or more at 0° C. The reaction mixture was adjusted to have a pH value of 10 by adding 1N aqueous NaOH solution and extracted with dichloromethane. The combined organic layer thus obtained was dried over anhydrous sodium sulfate, and concentrated under reduced pressure to obtain the title compound (46.5 g, 99%).

$^1$H-NMR Spectrum (300 MHz, CDCl3): δ 8.80 (s, 1H), 8.24 (d, 1H), 7.80 (d, 1H), 7.66 (d, 1H), 7.56 (d, 1H), 2.55 (s, 3H)

Step (4): Preparation of 1-chloro-6-methyl-5-nitroisoquinoline

6-Methyl-5-nitroquinoline (46.5 g, 0.228 mol) obtained in Step (3) was dissolved in 1,2-dichloroethane (1.8 L), added with POCl$_3$ (107 mL, 1.14 mol) at room temperature, and refluxed for 7 hours or more. The reaction solution was cooled to room temperature and concentrated by distilling the solvent under reduced pressure. The concentrated solid was dissolved in dichloromethane, added with an ice water, and extracted with dichloromethane. The combined organic layer was dried over anhydrous sodium sulfate, filtered, and concentrated under reduced pressure. The concentrated solid was added with a mixed solution of ethyl acetate/hexane=1/1 (v/v), and stirred for 2 hours or more at room temperature. The solid thus obtained was filtered under reduced pressure, and washed with a mixed solution of ethyl acetate/hexane=1/1 (v/v). The filtered solid was dried with warm wind in an oven (40° C.) for over 3 hours or more to obtain the title compound (28 g, 55%).

$^1$H-NMR Spectrum (300 MHz, DMSO-d$_6$): δ 8.53 (m, 2H), 7.92 (d, 1H), 7.67 (d, 1H), 2.72 (s, 3H)

Example 1

Preparation of 1-amino-N-(2-methyl-5-(3-(trifluoromethyl)benzamido)phenyl)isoquinoline-5-carboxamide

Step (1): Preparation of N-(4-methyl-3-nitrophenyl)-3-(trifluoromethyl)benzamide 4-Methyl-3-nitroaniline (5 g, 32.9 mmol) was stirred in a solvent of dichloromethane (150 mL). The reaction solution was added with DIPEA (11.48 mL, 65.7 mmol) and 3-(trifluoromethyl)benzoylchloride (4.86 mL, 32.9 mmol), and stirred for about an hour at room temperature. The reaction mixture was washed with 1M aqueous HCl solution, an aqueous sodium bicarbonate and saline. The organic layer was dried over anhydrous sodium sulfate, filtered, and concentrated under reduced pressure to obtain the title compound (10.6 g, 99%).

$^1$H-NMR Spectrum (300 MHz, DMSO-$d_6$): δ 10.8 (s, 1H), 8.53 (s, 1H), 8.32 (m, 2H), 8.03 (m, 2H), 7.84 (t, 1H), 7.53 (d, 1H).

MS (ESI$^+$, m/z): 325 [M+H]$^+$

Step (2): Preparation of N-(3-amino-4-methylphenyl)-3-(trifluoromethyl)benzamide N-(4-Methyl-3-nitrophenyl)-3-(trifluoromethyl)benzamide (10.6 g, 32.7 mmol) obtained in Step (1) was stirred in a solvent of methanol. The reaction solution was mixed with Pd/C (1 g, 9.40 mmol), followed by stirring under hydrogen conditions for about 2 hours at room temperature. The reaction mixture was filtered through a Celite pad under reduced pressure, and washed with methanol. The filtrate was concentrated under reduced pressure to obtain the title compound (8.9 g, 93%).

$^1$H-NMR Spectrum (300 MHz, DMSO-$d_6$): δ 8.24 (s, 2H), 7.93 (s, 1H), 7.77 (d, 1H), 7.10 (s, 1H), 6.85 (d, 2H), 4.90 (s, 2H), 2.02 (s, 3H).

MS (ESI$^+$, m/z): 295 [M+H]$^+$

Step (3): Preparation of 1-(t-butylamino)-N-(2-methyl-5-(3-(trifluoromethyl)benzamido)phenyl)isoquinoline-5-carboxamide 1-(t-Butylamino)isoquinoline-5-carboxylic acid (0.33 g, 1.35 mmol) obtained in Step (6) of Preparation Example 1 was dissolved in dimethyl formamide (3 mL), added with HATU (0.62 g, 1.62 mmol) and DIPEA (0.47 mL, 2.70 mmol), and stirred for 10 minutes. The reaction mixture was added with N-(3-amino-4-methylphenyl)-3-(trifluoromethyl)benzamide (0.40 g, 1.35 mmol) obtained in Step (2) above, and stirred for 12 hours or more at room temperature. The reaction mixture was diluted with ethyl acetate, and washed with a saturated sodium bicarbonate solution and saline. The organic layer thus obtained was dried over anhydrous sodium sulfate, filtered, and concentrated under reduced pressure. The concentrated compound was purified using silica gel chromatography to obtain the title compound (0.13 g, 18%).

MS (ESI$^+$, m/z): 521.21 [M+H]$^+$

Step (4): Preparation of 1-amino-N-(2-methyl-5-(3-(trifluoromethyl)benzamido)phenyl)isoquinoline-5-carboxamide 1-(t-Butylamino)-N-(2-methyl-5-(3-(trifluoromethyl) benzamido)phenyl)isoquinoline-5-carboxamide (0.13 g, 0.25 mmol) obtained in Step (3) above was dissolved in tetrahydrofuran (1 mL), slowly added with TFA (3 mL) at 0° C., and stirred for about 4 hours at 70° C. The reaction mixture was cooled to room temperature, and adjusted to have a pH value in a range of 10~11 by adding a saturated aqueous sodium bicarbonate solution. The reaction mixture was diluted with ethyl acetate, followed by washing with distilled water. The organic layer thus obtained was dried over anhydrous sodium sulfate, filtered, and concentrated under reduced pressure. The concentrated compound was purified using silica gel chromatography to obtain the title compound (10 mg, 8%).

$^1$H-NMR Spectrum (300 MHz, DMSO-$d_6$): δ 10.61 (s, 1H), 10.11 (s, 1H), 8.29 (m, 3H), 7.92 (m, 4H), 7.75 (t, 1H), 7.58 (d, 1H), 7.52 (t, 1H), 7.22 (d, 1H), 7.15 (d, 1H), 6.87 (s, 2H), 2.20 (s, 3H).

MS (ESI$^+$, m/z): 465 [M+H]$^+$

Example 2

Preparation of 1-(t-butylamino)-N-(2-methyl-5-((3-(trifluoromethyl)phenyl)carbamoyl)phenyl)isoquinoline-5-carboxamide

Step (1): Preparation of 4-methyl-3-nitro-N-(3-(trifluoromethyl)phenyl)benzamide 4-Methyl-3-nitrobenzoic acid (14.6 g, 81.0 mmol) was stirred in a solvent of dimethyl formamide (40 mL). The reaction solution was added with HATU (47.2 g, 124 mmol), DIPEA (32.5 mL, 186 mmol) and 3-(trifluoromethyl)aniline (7.72 mL, 62.1 mmol), followed by stirring for about 12 hours at room temperature. The reaction mixture was diluted with ethyl acetate, and washed with a saturated aqueous sodium bicarbonate solution and saline. The organic layer thus obtained was dried over anhydrous sodium sulfate, filtered, and concentrated under reduced pressure. The concentrated solid was added with ethyl acetate, and stirred for 2 hours or more. The resulting solid was filtered under reduced pressure, and washed with ethyl acetate and methanol. The filtered solid was dried with warm wind in an oven (40° C.) for 3 hours or more to obtain the title compound (14.9 g, 74%).

$^1$H-NMR Spectrum (300 MHz, DMSO-$d_6$): δ 10.75 (s, 1H), 8.60 (s, 1H), 8.24 (m, 2H), 8.07 (d, 1H), 7.72 (d, 1H), 7.65 (t, 1H), 7.50 (d, 1H), 2.68 (s, 3H).

MS (ESI$^+$, m/z): 325 [M+H]$^+$

Step (2): Preparation of 3-amino-4-methyl-N-(3-(trifluoromethyl)phenyl)benzamide The procedures of Step (2) of Example 1 were repeated, except for using 4-methyl-3-nitro-N-(3-(trifluoromethyl)phenyl)benzamide obtained in Step (1) above to obtain the title compound (9.1 g, 67%).

$^1$H-NMR Spectrum (300 MHz, DMSO-$d_6$): δ 10.30 (s, 1H), 8.24 (s, 1H), 8.03 (d, 1H), 7.57 (d, 1H), 7.41 (d, 1H), 7.17 (t, 1H), 7.08 (m, 2H), 5.10 (s, 2H), 2.12 (s, 3H).

MS (ESI$^+$, m/z): 295 [M+H]$^+$

Step (3): Preparation of 1-(t-butylamino)-N-(2-methyl-5-((3-(trifluoromethyl)phenyl)carbamoyl)phenyl)isoquinoline-5-carboxamide The procedures of Step (3) of Example 1 were repeated, except for using 1-(t-butylamino)isoquinoline-5-carboxylic acid (0.33 g, 1.35 mmol) obtained in Step (6) of Preparation Example 1 and 3-amino-4-methyl-N-(3-(trifluoromethyl)

phenyl)benzamide obtained in Step (2) above to obtain the title compound (88 mg, 100%).
MS (ESI+, m/z): 521 [M+H]+

Example 3

Preparation of 1-amino-N-(2-methyl-5-((3-(trifluoromethyl)phenyl)carbamoyl)phenyl)isoquinoline-5-carboxamide The procedures of Step (4) of Example 1 were repeated, except for using 1-(t-butylamino)-N-(2-methyl-5-((3-(trifluoromethyl)phenyl)carbamoyl)phenyl)isoquinoline-5-carboxamide obtained in Step (3) of Example 2 to obtain the title compound (5.0 mg, 11%).
$^1$H-NMR Spectrum (300 MHz, DMSO-$d_6$): δ 10.66 (s, 1H), 10.38 (s, 1H), 8.41 (d, 1H), 8.26 (s, 1H), 8.10 (s, 2H), 8.00 (d, 1H), 7.87 (m, 2H), 7.65 (m, 3H), 7.49 (m, 2H), 7.29 (d, 1H), 7.20 (d, 1H), 2.40 (s, 3H).
MS (ESI+, m/z): 465 [M+H]+

Example 4

Preparation of 1-amino-N-(5-((4-chloro-3-(trifluoromethyl)phenyl)carbamoyl)-2-methylphenyl)isoquinoline-5-carboxamide The procedures of Steps (1), (2) and (3) of Example 2 and Step (4) of Example 1 were repeated step by step, except for using 4-chloro-3-(trifluoromethyl)aniline instead of aniline in Step (1) of Example 2 to obtain the title compound (30 mg, 24%).
$^1$H-NMR Spectrum (300 MHz, DMSO-$d_6$): δ 10.66 (s, 1H), 10.19 (s, 1H), 8.38 (m, 2H), 8.13 (m, 2H), 7.89 (m, 3H), 7.72 (d, 1H), 7.58 (m, 1H), 7.47 (d, 1H), 7.25 (d, 1H), 6.93 (s, 2H), 2.43 (s, 3H).
MS (ESI+, m/z): 499 [M+H]+

Example 5

Preparation of 1-amino-N-(5-((3-(2-cyanopropan-2-yl)phenyl)carbamoyl)-2-methylphenyl)isoquinoline-5-carboxamide Step (1): Preparation 2-methyl-2-(3-nitrophenyl)propanenitrile NaH (4.34 g, 90.4 mmol) was stirred in a solvent of tetrahydrofuran (20 mL) at 0° C. The reaction solution was slowly added with 2-(3-nitrophenyl)acetonitrile (2.2 g, 13.6 mmol), and stirred for about 30 minutes at 0° C. The reaction solution was added with MeI (6.67 mL, 107 mmol), followed by stirring for about 12 hours at room temperature. The reaction mixture was added with an ice water. The organic layer was separated out and the aqueous layer was extracted with ethyl acetate. The organic layer was dried over anhydrous sodium sulfate, filtered, and concentrated under reduced pressure. The concentrated compound was purified using silica gel chromatography (EA:HEX=1:9) to obtain the title compound (0.6 g, 23%).
$^1$H-NMR Spectrum (300 MHz, DMSO-$d_6$): δ 8.33 (s, 1H), 8.22 (d, 1H), 7.91 (d, 1H), 7.65 (t, 1H), 1.81 (s, 6H).
MS (ESI+, m/z): 191 [M+H]+

Step (2): Preparation of 2-(3-aminophenyl)-2-methylpropanenitrile

2-Methyl-2-(3-nitrophenyl)propanenitrile (0.6 g, 3.15 mmol) obtained in Step (1) above was stirred in a solvent of methanol. The reaction solution was mixed with Pd/C (0.06 g, 0.56 mmol), followed by stirring under hydrogen conditions for about 2 hours at room temperature. The reaction mixture was filtered through a Celite pad under reduced pressure, and washed with methanol. The filtrate was concentrated under reduced pressure to obtain the title compound (0.48 g, 95%).
$^1$H-NMR Spectrum (300 MHz, DMSO-$d_6$): δ 7.06 (t, 1H), 6.71 (s, 1H), 6.61 (d, 1H), 6.52 (d, 1H), 5.21 (s, 2H), 1.61 (s, 6H).
MS (ESI+, m/z): 161 [M+H]+

Step (3): Preparation of 1-amino-N-(5-((3-(2-cyanopropan-2-yl)phenyl)carbamoyl)-2-methylphenyl)isoquinoline-5-carboxamide The procedures of Steps (1), (2) and (3) of Example 2 and Step (4) of Example 1 were repeated step by step, except for using 2-(3-aminophenyl)-2-methylpropanenitrile obtained in Step (2) above instead of aniline in Step (1) of Example 2 to obtain the title compound (14 mg, 20%).
$^1$H-NMR Spectrum (300 MHz, DMSO-$d_6$): δ 10.36 (s, 1H), 10.15 (s, 1H), 8.35 (m, 1H), 8.07 (m, 1H), 7.91 (m, 5H), 7.56 (m, 1H), 7.43 (m, 2H), 7.24 (m, 2H), 6.90 (s, 2H), 2.38 (s, 3H), 1.69 (s, 6H).
MS (ESI+, m/z): 464 [M+H]

Example 6

Preparation of 1-(t-butylamino)-N-(5-((4-((4-ethylpiperazin-1-yl)methyl)-3-(trifluoromethyl)phenyl)carbamoyl)-2-methylphenyl)isoquinoline-5-carboxamide Step (1): Preparation of 1-(bromomethyl)-4-nitro-2-(trifluoromethyl)benzene 1-Methyl-4-nitro-2-(trifluoromethyl)benzene (25 g, 122 mmol) was stirred in a solvent of dichloethane (300 mL). The reaction solution was added with NBS (21.7 g, 122 mmol) and AIBN (2.0 g, 12.2 mmol), followed by stirring for about 12 hours at 80° C. The solid thus obtained was filtered under reduced pressure and dried with warm wind in an oven (40° C.) for 3 hours or more to obtain the title compound (34 g, 98%).
$^1$H-NMR Spectrum (300 MHz, DMSO-$d_6$): δ 8.53 (d, 1H), 8.42 (s, 1H), 8.06 (d, 1H), 4.88 (s, 2H).
MS (ESI+, m/z): 283 [M+H]

Step (2): Preparation of 1-ethyl-4-(4-nitro-2-(trifluoromethyl)benzyl)piperazine 1-(Bromomethyl)-4-nitro-2-(trifluoromethyl)benzene (34 g, 120 mmol) obtained in Step (1) above was stirred in a solvent of dichloromethane (300 mL). The reaction solution was added with 1-ethylpiperazine (15.97 mL, 126 mmol) and DIPEA (27.2 mL, 156 mmol), followed by stirring for about 3 hours at room temperature. The reaction mixture was diluted with dichloromethane, washed with a saturated aqueous sodium bicarbonate solution and saline. The organic layer thus obtained was dried over anhydrous sodium sulfate, filtered, and concentrated under reduced pressure to obtain the title compound (21.7 g, 57%).
$^1$H-NMR Spectrum (300 MHz, DMSO-$d_6$): δ 8.52 (d, 1H), 8.40 (s, 1H), 8.09 (d, 1H), 3.71 (s, 2H), 2.35 (m, 10H), 1.00 (t, 3H).
MS (ESI+, m/z): 318 [M+H]

Step (3): Preparation of 4-((4-ethylpiperazin-1-yl)methyl)-3-(trifluoromethyl)aniline 1-Ethyl-4-(4-nitro-2-(trifluoromethyl)benzyl)piperazine (21.7 g, 68.3 mmol) obtained in Step (2) above was stirred in a solution of methanol. The reaction solution was mixed with Pd/C (1.8 g, 17.08 mmol), followed by stirring under hydrogen conditions for about 12 hours at room temperature. The reaction mixture was filtered through a Celite pad under reduced pressure, and washed with methanol. The filtrate was concentrated under reduced pressure to obtain the title compound (19.4 g, 99%).

$^1$H-NMR Spectrum (300 MHz, DMSO-$d_6$): δ 7.30 (d, 1H), 6.85 (s, 1H), 6.76 (d, 1H), 5.42 (s, 2H), 3.37 (s, 2H), 2.33 (m, 10H), 1.01 (t, 3H).

MS (ESI$^+$, m/z): 288 [M+H]$^+$

Step (4): Preparation of 1-(t-butylamino)-N-(5-((4-((4-ethylpiperazin-1-yl)methyl)-3-(trifluoromethyl)phenyl)carbamoyl)-2-methylphenyl)isoquinoline-5-carboxamide The procedures of Steps (1), (2) and (3) of Example 2 were repeated step by step, except for using 4-((4-ethylpiperazin-1-yl)methyl)-3-(trifluoromethyl)aniline obtained in Step (3) above instead of aniline in Step (1) of Example 2 to obtain the title compound (0.032 g, 12%).

MS (ESI$^+$, m/z): 647 [M+H]

Example 7

Preparation of 1-amino-N-(5-((4-((4-ethylpiperazin-1-yl)methyl)-3-(trifluoromethyl)phenyl)carbamoyl)-2-methylphenyl)isoquinoline-5-carboxamide The procedures of Step (4) of Example 1 were repeated, except for using 1-(t-butylamino)-N-(5-((4-((4-ethylpiperazin-1-yl)methyl)-3-(trifluoromethyl)phenyl)carbamoyl)-2-methylphenyl)isoquinoline-5-carboxamide obtained in Step (4) of Example 6 to obtain the title compound (3.0 mg, 11%).

MS (ESI$^+$, m/z): 591 [M+H]$^+$

Example 8

Preparation of 1-(t-butylamino)-N-(2-methyl-5-(phenylcarbamoyl)phenyl)isoquinoline-5-carboxamide The procedures of Steps (1), (2) and (3) of Example 2 were repeated step by step, except for using aniline instead of 3-trifluoro-aniline in Step (1) of Example 2 to obtain the title compound (1.2 mg, 3%).

MS (ESI$^+$, m/z): 453 [M+H]

Example 9

Preparation of 1-amino-N-(2-methyl-5-((4-(trifluoromethyl)pyridin-2-yl)carbamoyl)phenyl)isoquinoline-5-carboxamide The procedures of Steps (1), (2) and (3) of Example 2 and Step (4) of Example 1 were repeated step by step, except for using 2-amino-4-(trifluoromethyl)pyridine instead of aniline in Step (1) of Example 2 to obtain the title compound (3.5 mg, 7%).

$^1$H-NMR Spectrum (300 MHz, DMSO-$d_6$): δ 11.29 (s, 1H), 10.15 (s, 1H), 8.69 (m, 1H), 8.56 (m, 1H), 8.36 (m, 1H), 8.22 (m, 1H), 7.91 (m, 3H), 7.55 (m, 2H), 7.46 (d, 1H), 7.26 (d, 1H), 6.92 (s, 2H), 2.27 (s, 3H).

MS (ESI$^+$, m/z): 466 [M+H]

Example 10

Preparation of 1-amino-N-(5-((4,6-dimethylpyridin-2-yl)carbamoyl)-2-methylphenyl)isoquinoline-5-carboxamide The procedures of Steps (1), (2) and (3) of Example 2 and Step (4) of Example 1 were repeated step by step, except for using 2-amino-4,6-dimethylpyridine instead of aniline in Step (1) of Example 2 to obtain the title compound (2.8 mg, 8%).

$^1$H-NMR Spectrum (300 MHz, DMSO-$d_6$): δ 10.59 (s, 1H), 10.13 (s, 1H), 8.36 (d, 1H), 8.17 (s, 1H), 7.93 (d, 1H), 7.88 (m, 3H), 7.57 (t, 1H), 7.41 (d, 1H), 7.25 (d, 1H), 6.92 (s, 2H), 6.87 (s, 1H), 2.43 (s, 3H), 2.31 (s, 3H), 2.26 (s, 3H).

MS (ESI$^+$, m/z): 426 [M+H]

Example 11

Preparation of 1-amino-N-(2-methyl-5-((3-(4-methyl-1H-imidazol-1-yl)-5-(trifluoromethyl)phenyl)carbamoyl)phenyl)isoquinoline-5-carboxamide

Step (1): Preparation of 3-(4-methyl-1H-imidazol-1-yl)-5-(trifluoromethyl)aniline 3-Bromo-5-(trifluoromethyl)aniline (0.2 mL, 1.43 mmol) was stirred in a solvent of dimethylacetamide (10 mL). The reaction solution was added with 4-methyl-1H-imidazole (0.35 g, 4.26 mmol), $K_2CO_3$ (0.20 g, 5.23 mmol), Cu (0.022 g, 0.346 mmol) and CuI (0.068 g, 0.115 mmol), and stirred for about 2 days at 140° C. The reaction mixture was diluted with ethyl acetate, and washed with a saturated aqueous sodium bicarbonate solution and saline. The organic layer thus obtained was dried over anhydrous sodium sulfate, filtered, and concentrated under reduced pressure to obtain the title compound (0.23 g, 67%).

$^1$H-NMR Spectrum (300 MHz, DMSO-$d_6$): δ 8.06 (s, 1H), 7.36 (s, 1H), 6.96 (s, 1H), 6.92 (s, 1H), 6.80 (s, 1H), 5.86 (s, 2H), 2.14 (s, 3H).

MS (ESI$^+$, m/z): 242 [M+H]$^+$

Step (2): Preparation of 1-amino-N-(2-methyl-5-((3-(4-methyl-1H-imidazol-1-yl)-5-(trifluoromethyl)phenyl)carbamoyl)phenyl)isoquinoline-5-carboxamide The procedures of Steps (1), (2) and (3) of Example 2 and Step (4) of Example 1 were repeated step by step, except for using 3-(4-methyl-1H-imidazol-1-yl)-5-(trifluoromethyl)aniline obtained in Step (1) above instead of aniline in Step (1) of Example 2 to obtain the title compound (3.0 mg, 7.5%).

$^1$H-NMR Spectrum (300 MHz, DMSO-$d_6$): δ 10.73 (s, 1H), 10.38 (s, 1H), 8.92 (m, 2H), 8.68 (d, 1H), 8.56 (s, 1H), 8.37 (s, 1H), 8.28 (d, 1H), 8.17 (m, 2H), 7.92 (m, 2H), 7.77 (m, 2H), 7.62 (s, 1H), 7.49 (m, 2H), 2.39 (s, 3H), 2.21 (s 3H).

MS (ESI$^+$, m/z): 545 [M+H]

Example 12

Preparation of 1-(t-butylamino)-N-(5-(3-(4-chloro-3-(trifluoromethyl)phenyl)ureido)-2-methylphenyl)isoquinoline-5-carboxamide Step (1): Preparation of 1-(4-chloro-3-(trifluoromethyl)phenyl)-3-(4-methyl-3-nitrophenyl)urea 1-Chloro-4-isocyanato-2-(trifluoromethyl)benzene (9.97 g, 45.0 mmol) was stirred in a solvent of tetrahydrofuran (100 mL). The reaction solution was added with 4-methyl-3-nitroaniline (6.52 g, 42.9 mmol), followed by stirring for about 6 hours at room temperature. The reaction mixture was diluted with ethyl acetate, and washed with a saturated aqueous sodium bicarbonate solution and saline. The organic layer thus obtained was dried over anhydrous sodium sulfate and concentrated under reduced pressure. The concentrated solid was added with a mixed solution of ethyl acetate/hexane (1/5), followed by stirring for 2 hours or more. The resulting solid was filtered under reduced pressure, and washed with diethyl ether. The filtered solid was dried with warm wind in an oven (40° C.) for 3 hours or more to obtain the title compound (14 g, 87%).

$^1$H-NMR Spectrum (300 MHz, DMSO-d$_6$): δ 9.28 (s, 2H), 8.27 (d, 1H), 8.10 (d, 1H), 7.69 (m, 3H), 7.42 (d, 1H), 2.45 (s, 3H).

MS (ESI$^+$, m/z): 374 [M+H]

Step (2): Preparation of 1-(3-amino-4-methylphenyl)-3-(4-chloro-3-(trifluoromethyl)phenyl)urea 1-(4-Chloro-3-(trifluoromethyl)phenyl)-3-(4-methyl-3-nitrophenyl)urea (7 g, 18.7 mmol) obtained in Step (1) above was stirred in a solvent of ethanol (100 mL). The reaction solution was added with tin chloride (II) dihydrate (12.68 g, 56.2 mmol), followed by stirring for about 4 hours at 80° C. The reaction mixture was diluted with ethyl acetate, and washed with a saturated aqueous sodium bicarbonate solution and saline. The organic layer thus obtained was dried over anhydrous sodium sulfate, filtered, and concentrated under reduced pressure. The concentrated solid was added with a mixed solution of ethyl acetate/hexane (1/1), and stirred for 2 hours or more. The resulting solid was filtered under reduced pressure, washed with diethyl ether, and the filtered solid was dried with warm wind in an oven (40° C.) for 3 hours or more to obtain the title compound (3.9 g, 61%).

$^1$H-NMR Spectrum (300 MHz, DMSO-d$_6$): δ 8.97 (s, 1H), 8.43 (s, 1H), 8.16 (s, 1H), 7.59 (s, 2H), 6.81 (dd, 2H), 6.52 (dd, 1H), 5.02 (s, 2H), 1.97 (s, 3H).

MS (ESI$^+$, m/z): 344 [M+H]

Step (3): Preparation 1-(t-butylamino) N (5 (3 (4 chloro-3-(trifluoromethyl)phenyl)ureido)-2-methylphenyl)isoquinoline-5-carboxamide The procedures of Step (3) of Example 1 were repeated, except for using 1-(3-amino-4-methylphenyl)-3-(4-chloro-3-(trifluoromethyl)phenyl)urea instead of aniline in Step (3) of Example 1 to obtain the title compound (50 mg, 41%).

MS (ESI$^+$, m/z): 570 [M+H]

Example 13

Preparation of 1-amino-N-(5-(3-(4-chloro-3-(trifluoromethyl)phenyl)ureido)-2-methylphenyl)isoquinoline-5-carboxamide The procedures of Step (4) of Example 1 were repeated, except for using 1-(t-butylamino)-N-(5-(3-(4-chloro-3-(trifluoromethyl)phenyl)ureido)-2-methylphenyl)isoquinoline-5-carboxamide obtained in Step (3) of Example 12 to obtain the title compound (23 mg, 45%).

$^1$H-NMR Spectrum (300 MHz, DMSO-d$_6$): δ 10.60 (s, 1H), 9.48 (s, 1H), 9.12 (s, 1H), 8.52 (d, 1H), 8.04 (m, 1H), 7.98 (m, 1H), 7.85 (d, 1H), 7.63 (m, 3H), 7.53 (m, 2H), 7.30 (m, 2H), 7.20 (d, 1H), 2.43 (s, 3H).

MS (ESI$^+$, m/z): 514 [M+H]$^+$

Example 14

Preparation of 1-amino-N-(2-methyl-5-(3-(3-(trifluoromethyl)phenyl)ureido)phenyl)isoquinoline-5-carboxamide The procedures of Steps (1), (2) and (3) of Example 12 and Step (4) of Example 1 were repeated step by step, except for using 1-isocyanato-3-(trifluoromethyl)benzene instead of benzene in Step (1) of Example 12 to obtain the title compound (4.0 mg, 9%).

$^1$H-NMR Spectrum (300 MHz, DMSO-d$_6$): δ 9.89 (s, 1H), 8.94 (s, 1H), 8.79 (m, 1H), 8.24 (m, 1H), 7.94 (m, 1H), 7.79 (m, 2H), 7.56 (m, 1H), 7.45 (m, 3H), 7.20 (m, 2H), 7.10 (m, 2H), 6.83 (s, 2H), 2.20 (s, 3H).

MS (ESI$^+$, m/z): 480 [M+H]

Example 15

Preparation of 1-(t-butylamino)-N-(5-(3-(2-fluoro-5-(trifluoromethyl)phenyl)ureido)-2-methylphenyl)isoquinoline-5-carboxamide The procedures of Steps (1), (2) and (3) of Example 12 were repeated step by step, except for using 1-fluoro-2-isocyanato-4-trifluoromethyl benzene instead of benzene in Step (1) of Example 12 to obtain the title compound (60 mg, 42%).

MS (ESI$^+$, m/z): 554 [M+H]

Example 16

Preparation 1-amino-N-(5-(3-(2-fluoro-5-(trifluoromethyl)phenyl)ureido)-2-methylphenyl)isoquinoline-5-carboxamide The procedures of Step (4) of Example 1 were repeated, except for using 1-(t-butyl)-N-(5-(3-(2-fluoro-5-(trifluoromethyl)phenyl)ureido)-2-methylphenyl)isoquinoline-5-carboxamide obtained in Example 15 to obtain the title compound (62 mg, 43%).

MS (ESI$^+$, m/z): 498 [M+H]$^+$

Example 17

Preparation of 1-amino-N-(3-((3-(trifluoromethyl)phenyl)carbamoyl)phenyl)isoquinoline-5-carboxamide The procedures of Steps (1), (2) and (3) of Example 2 and Step (4) of Example 1 were repeated step by step, except for using 3-nitrobenzoic acid instead of benzoic acid in Step (1) of Example 2 to obtain the title compound (10 mg, 11%).

$^1$H-NMR Spectrum (300 MHz, DMSO-d$_6$): δ 10.81 (s, 1H), 10.47 (s, 1H), 8.38 (d, 1H), 8.27 (s, 1H), 8.08 (m, 3H), 7.93 (d, 2H), 7.87 (d, 2H), 7.63 (m, 2H), 7.46 (d, 1H), 7.13 (d, 1H), 6.94 (s, 2H).

MS (ESI$^+$, m/z): 451 [M+H]

Example 18

Preparation of 1-amino-N-(6-methyl-1-((3-(trifluoromethyl)phenyl)amino)isoquinolin-5-yl)isoquinoline-5-carboxamide Step (1): Preparation of 6-methyl-5-nitro-N-(3-(trifluoromethyl)phenyl)isoquinoline-1-amine 1-Chloro-6-methyl-5-nitroquinoline (1 g, 4.50 mmol) obtained in Step (4) of Preparation Example 2 was dissolved in 2-propanol (20 mL), and added with 3-(trifluoromethyl)aniline (0.61 mL, 4.95 mmol) at room temperature. The reaction solution was sealed in a container, and stirred for 12 hours or more at 90° C. The temperature of the reaction mixture was cooled to room temperature. The solid thus obtained was filtered under reduced pressure, and washed with ethyl acetate. The filtered solid was dried with warm wind in an oven (40° C.) for 3 hours or more to obtain the title compound (1.47 g, 94%).
$^1$H-NMR Spectrum (300 MHz, DMSO-$d_6$): δ 11.07 (s, 1H), 9.03 (d, 1H), 8.16 (s, 1H), 8.08 (d, 1H), 7.93 (d, 1H), 7.82 (d, 1H), 7.69 (t, 1H), 7.56 (s, 1H), 6.95 (d, 1H).
MS (ESI$^+$, m/z): 348 [M+H]$^+$ Step (2): Preparation of 6-methyl-N$^1$-(3-(trifluoromethyl)phenyl)isoquinoline-1,5-diamine 6-Methyl-5-nitro-N-(3-(trifluoromethyl)phenyl)isoquinoline-1-amine (1.49 g, 4.29 mmol) obtained in Step (1) above was stirred in a solvent of ethanol (10 mL). The reaction solution was added with tin chloride (II) dihydrate (4.06 g, 21.46 mmol), and stirred for about 5 hours at 90° C. The reaction mixture was diluted with ethyl acetate, and washed with a saturated aqueous sodium bicarbonate solution and saline. The organic layer thus obtained was dried over anhydrous sodium sulfate, filtered, and concentrated under reduced pressure to obtain the title compound (0.42 g, 31%).
$^1$H-NMR Spectrum (300 MHz, DMSO-$d_6$): δ 9.15 (s, 1H), 8.34 (s, 1H), 8.21 (d, 1H), 7.88 (m, 2H), 7.66 (d, 1H), 7.49 (m, 2H), 7.28 (d, 1H), 5.53 (s, 2H), 2.25 (s, 3H).
MS (ESI$^+$, m/z): 318 [M+H]$^+$ Step (3): Preparation of 1-amino-N-(6-methyl-1-((3-(trifluoromethyl)phenyl)amino)isoquinolin-5-yl)isoquinoline-5-carboxamide The procedures of Steps (3) and (4) of Example 2 were repeated step by step, except for using 6-methyl-N$^1$-(3-(trifluoromethyl)phenyl)isoquinoline-1,5-diamine obtained in Step (2) above instead of aniline in Step (3) of Example 1 to obtain the title compound (1.0 mg, 2%).
MS (ESI$^+$, m/z): 488 [M+H]$^+$

Example 19

Preparation of 1-((5-methoxypyridin-2-yl)amino)-N-(2-methyl-5-(3-(trifluoromethyl)benzamido)phenyl)isoquinoline-5-carboxamide Step (1): Preparation of methyl 1-chloroisoquinoline-5-carboxylate 5-(Methoxycarbonyl)isoquinoline 2-oxide (2 g, 9.84 mmol) obtained in Step (4) of Preparation Example 1 was dissolved in dichloromethane (20 mL), added with POCl$_3$ (20 mL) at room temperature, and stirred for 4 hours or more at 90° C. The temperature of the reaction mixture was lowered to room temperature, followed by quenching with distilled water. The reaction mixture was diluted with dichloromethane, and washed with a saturated aqueous sodium bicarbonate solution and saline. The organic layer thus obtained was dried over anhydrous sodium sulfate, filtered, and concentrated under reduced pressure to obtain the title compound (1.86 g, 86%).
$^1$H-NMR Spectrum (300 MHz, DMSO-d6): δ 8.64 (d, 1H), 8.59 (d, 1H), 8.49 (d, 1H), 8.44 (d, 1H), 7.94 (t, 1H), 3.97 (s, 3H).
MS (ESI$^+$, m/z): 222 [M+H]$^+$ Step (2): Preparation of methyl 1-((5-methoxypyridin-2-yl)amino)isoquinoline-5-carboxylate Methyl 1-chloroisoquinoline-5-carboxylate (0.5 g, 2.26 mmol) obtained in Step (1) above was dissolved in 2-propanol (5 mL), and added with 5-amino-p-methoxyaniline (0.33 g, 2.74 mmol) at room temperature. The reaction solution was sealed and stirred for 4 hours or more at 90° C. The reaction mixture was cooled to room temperature, and the solvent was distilled under reduced pressure. The concentrated solid was added with diethyl ether, the solid thus obtained was filtered under reduced pressure. The resulting solid was dried with warm wind in an oven (40° C.) for 3 hours or more to obtain the title compound (0.42 g, 61%).
$^1$H-NMR Spectrum (300 MHz, DMSO-$d_6$): δ 11.07 (s, 1H), 9.04 (d, 1H), 8.49 (d, 1H), 8.40 (s, 1H), 8.01 (m, 3H), 7.77 (d, 1H), 7.02 (dd, 1H), 3.95 (s, 3H), 3.84 (s, 3H).
MS (ESI$^+$, m/z): 310 [M+H]$^+$ Step (3): Preparation of 1-((5-methoxypyridin-2-yl)amino)isoquinoline-5-carboxylic acid The procedures of Steps (6) of Example 1 were repeated, except for using methyl 1-((5-methoxypyridin-2-yl)amino)isoquinoline-5-carboxylate obtained in Step (2) above instead of carboxylate in Step (6) of Example 1 to obtain the title compound (0.11 g, 50%).
$^1$H-NMR Spectrum (300 MHz, CDCl$_3$): δ 11.25 (s, 1H), 9.01 (d, 1H), 8.56 (d, 1H), 8.41 (s, 1H), 8.17 (d, 1H), 7.93 (m, 2H), 7.74 (d, 1H), 7.07 (d, 1H), 3.93 (s, 3H).
MS (ESI$^+$, m/z): 296 [M+H]$^+$ Step (4): Preparation of 1-((5-methoxypyridin-2-yl)amino)-N-(2-methyl-5-(3-(trifluoromethyl)benzamido)phenyl)iso quinoline-5-carboxamide The procedures of Step (3) of Example 1 were repeated, except for using 1-((5-methoxypyridin-2-yl)amino)isoquinoline-5-carboxylic acid obtained in Step (3) above instead of carboxylic acid in Step (3) of Example 1 (18 mg, 22%).
$^1$H-NMR Spectrum (300 MHz, CDCl$_3$): δ 10.51 (s, 1H), 10.12 (s, 1H), 9.29 (s, 1H), 8.65 (d, 1H), 8.54 (s, 1H), 8.33 (d, 1H), 8.14 (d, 1H), 8.02 (m, 4H), 7.96 (m, 4H), 7.44 (d, 1H), 7.30 (d, 1H), 6.86 (d, 1H), 3.85 (s, 3H), 2.31 (s, 3H).
MS (ESI$^+$, m/z): 572 [M+H]$^+$

Example 20

Preparation of 1-((5-methoxypyridin-2-yl)amino)-N-(2-methyl-5-(3-(3-(trifluoromethyl)phenyl)ureido)phenyl)isoquinoline-5-carboxamide The procedures of Example 18 were repeated, except for using 1-((5-methoxypyridin-2-yl)amino)isoquinoline-5-carboxylic acid obtained in Step (3) of Example 19 and 1-(3-amino-4-methylphenyl)-3-(3-(trifluoromethyl)phenyl)urea obtained in Example 14 instead of carboxylic acid and aniline in Step (3) of Example 1 to obtain the title compound (48 mg, 65%).

$^1$H-NMR Spectrum (300 MHz, CDCl$_3$): δ 10.03 (s, 1H), 9.26 (s, 1H), 8.98 (s, 1H), 8.83 (s, 1H), 8.63 (d, 1H), 8.51 (s, 1H), 8.11 (d, 1H), 8.01 (m, 2H), 7.77 (m, 2H), 7.54 (m, 3H), 7.40 (m, 2H), 7.19 (d, 1H), 6.84 (d, 1H), 3.83 (s, 3H), 2.25 (s, 3H).

MS (ESI$^+$, m/z): 587 [M+H]$^+$

Example 21

Preparation of 1-((5-methoxypyridin-2-yl)amino)-N-(2-methyl-5-((3-(trifluoromethyl)phenyl)carbamoyl)phenyl)isoquinoline-5-carboxamide The procedures of Example 1 were repeated, except for using 1-((5-methoxypyridin-2-yl)amino)isoquinoline-5-carboxylic acid obtained in Step (3) of Example 19 and 3-amino-4-methyl-N-(3-(trifluoromethyl)phenyl)benzamide obtained in Example 3 instead of carboxylic acid and aniline in Step (3) of Example 1 to obtain the title compound (24 mg, 33%).

$^1$H-NMR Spectrum (300 MHz, CDCl$_3$): δ 10.55 (s, 1H), 10.24 (s, 1H), 9.25 (s, 1H), 8.62 (d, 1H), 8.51 (m, 2H), 8.24 (s, 1H), 8.09 (m, 4H), 7.82 (d, 1H), 7.74 (d, 1H), 7.59 (d, 1H), 7.47 (m, 3H), 6.81 (d, 1H), 3.83 (s, 3H), 2.34 (s, 3H).

MS (ESI$^+$, m/z): 572 [M+H]$^+$

Example 22

Preparation of N-(2-methyl-5-(3-(trifluoromethyl)benzamido)phenyl)isoquinoline-5-carboxamide The procedures of Example 1 were repeated, except for using isoquinoline-5-carboxylic acid instead of carboxylic acid in Step (3) of Example 1 to obtain the title compound (75 mg, 67%).

$^1$H-NMR Spectrum (300 MHz, CDCl$_3$): δ 10.70 (s, 1H), 10.52 (s, 1H), 9.43 (s, 1H), 8.62 (d, 1H), 8.33 (m, 3H), 8.14 (m, 2H), 7.96 (m, 2H), 7.82 (m, 2H), 7.67 (d, 1H), 7.31 (d, 1H), 2.34 (s, 3H).

MS (ESI$^+$, m/z): 450 [M+H]$^+$

Example 23

Preparation of N-(1-((4-chlorophenyl)amino)-6-methylisoquinolin-5-yl)isoquinoline-5-carboxamide Step (1): Preparation of N$^1$-(4-chlorophenyl)-6-methylisoquinoline-1,5-diamine The procedures of Steps (1) and (2) of Example 18 were repeated step by step, except for using 4-chloroaniline instead of aniline in Step (1) of Example 18 to obtain the title compound (0.83 g, 50%).

$^1$H-NMR Spectrum (300 MHz, DMSO-d$_6$): δ 8.95 (s, 1H), 7.95 (d, 2H), 7.88 (d, 1H), 7.63 (d, 1H), 7.43 (d, 1H), 7.33 (d, 2H), 7.26 (d, 1H), 5.48 (s, 2H), 2.25 (s, 3H).

MS (ESI$^+$, m/z): 284 [M+H]$^+$

Step (2): Preparation of N-(1-((4-chlorophenyl)amino)-6-methylisoquinolin-5-yl)isoquinoline-5-carboxamide The procedures of Example 18 were repeated, except for using N$^1$-(4-chlorophenyl)-6-methylisoquinoline-1,5-diamine obtained in Step (1) above instead of aniline in Example 22 to obtain the title compound (45 mg, 48%).

$^1$H-NMR Spectrum (300 MHz, DMSO-d$_6$): δ 10.51 (s, 1H), 9.45 (s, 1H), 9.33 (s, 1H), 8.64 (d, 1H), 8.49 (d, 1H), 8.37 (d, 2H), 8.21 (d, 1H), 8.07 (d, 2H), 7.90 (t, 1H), 7.66 (d, 1H), 7.39 (m, 3H), 2.50 (s, 3H).

MS (ESI$^+$, m/z): 439 [M+H]$^+$

The chemical structures of the compounds obtained in Examples 1 to 23 are shown in Table 1 below.

TABLE 1

| Example | Name | Formula |
|---|---|---|
| 1 | 1-amino-N-(2-methyl-5-(3-(trifluoromethyl)benzamido)phenyl)isoquinoline-5-carboxamide | |
| 2 | 1-(t-butylamino)-N-(2-methyl-5-((3-(trifluoromethyl)phenyl)carbamoyl)phenyl)isoquinoline-5-carboxamide | |
| 3 | 1-amino-N-(2-methyl-5-((3-(trifluoromethyl)phenyl)carbamoyl)phenyl)isoquinoline-5-carboxamide | |

TABLE 1-continued

| Example | Name | Formula |
|---|---|---|
| 4 | 1-amino-N-(5-((4-chloro-3-(trifluoromethyl)phenyl)carbamoyl)-2-methylphenyl)isoquinoline-5-carboxamide | |
| 5 | 1-amino-N-(5-((3-(2-cyanopropan-2-yl)phenyl)carbamoyl)-2-methylphenyl)isoquinoline-5-carboxamide | |
| 6 | 1-(t-butylamino)-N-(5-((4-((4-ethylpiperazin-1-yl)methyl)-3-(trifluoromethyl)phenyl)carbamoyl)-2-methylphenyl)isoquinoline-5-carboxamide | |
| 7 | 1-amino-N-(5-((4-((4-ethylpiperazin-1-yl)methyl)-3-(trifluoromethyl)phenyl)carbamoyl)-2-methylphenyl)isoquinoline-5-carboxamide | |
| 8 | 1-(t-butylamino)-N-(2-methyl-5-(phenylcarbamoyl)phenyl)isoquinoline-5-carboxamide | |
| 9 | 1-amino-N-(2-methyl-5-((4-(trifluoromethyl)pyridin-2-yl)carbamoyl)phenyl)isoquinoline-5-carboxamide | |

TABLE 1-continued

| Example | Name | Formula |
|---|---|---|
| 10 | 1-amino-N-(5-((4,6-dimethylpyridin-2-yl)carbamoyl)-2-methylphenyl)isoquinoline-5-carboxamide | |
| 11 | 1-amino-N-(2-methyl-5-((3-(4-methyl-1H-imidazol-1-yl)-5-(trifluoromethyl)phenyl)carbamoyl)phenyl)isoquinoline-5-carboxamide | |
| 12 | 1-(t-butylamino)-N-(5-(3-(4-chloro-3-(trifluoromethyl)phenyl)ureido)-2-methylphenyl)isoquinoline-5-carboxamide | |
| 13 | 1-amino-N-(5-(3-(4-chloro-3-(trifluoromethyl)phenyl)ureido)-2-methylphenyl)isoquinoline-5-carboxamide | |
| 14 | 1-amino-N-(2-methyl-5-(3-(3-(trifluoromethyl)phenyl)ureido)phenyl)isoquinoline-5-carboxamide | |
| 15 | 1-(t-butylamino)-N-(5-(3-(2-fluoro-5-(trifluoromethyl)phenyl)ureido)-2-methylphenyl)isoquinoline-5-carboxamide | |
| 16 | 1-amino-N-(5-(3-(2-fluoro-5-(trifluoromethyl)phenyl)ureido)-2-methylphenyl)isoquinoline-5-carboxamide | |

TABLE 1-continued

| Example | Name | Formula |
|---|---|---|
| 17 | 1-amino-N-(3-((3-(trifluoromethyl)phenyl)carbamoyl)phenyl)isoquinoline-5-carboxamide | 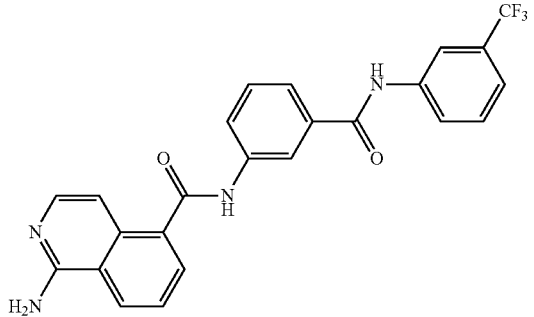 [SMILES: Nc1nccc2c(C(=O)Nc3cccc(C(=O)Nc4cccc(C(F)(F)F)c4)c3)cccc12] |
| 18 | 1-amino-N-(6-methyl-1-((3-(trifluoromethyl)phenyl)amino)isoquinolin-5-yl)isoquinoline-5-carboxamide | 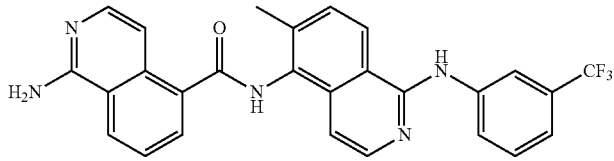 [SMILES: Cc1ccc2c(Nc3cccc(C(F)(F)F)c3)nccc2c1NC(=O)c1cccc2c(N)nccc12] |
| 19 | 1-((5-methoxypyridin-2-yl)amino)-N-(2-methyl-5-(3-(trifluoromethyl)benzamido)phenyl)isoquinoline-5-carboxamide | 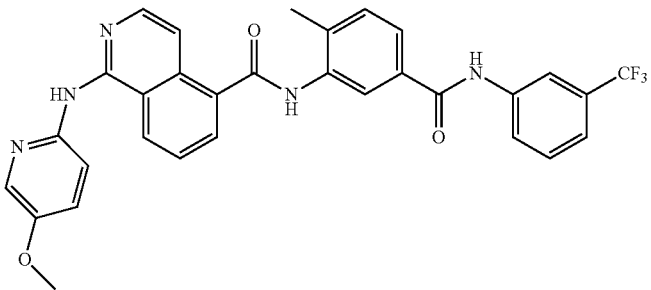 [SMILES: COc1ccc(Nc2nccc3c(C(=O)Nc4cc(C(=O)Nc5cccc(C(F)(F)F)c5)ccc4C)cccc23)nc1] |
| 20 | 1-((5-methoxypyridin-2-yl)amino)-N-(2-methyl-5-(3-(3-(trifluoromethyl)phenyl)ureido)phenyl)isoquinoline-5-carboxamide | 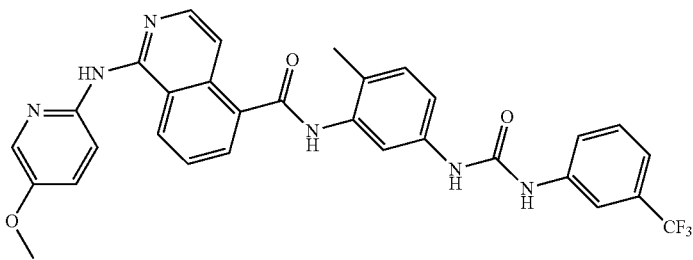 [SMILES: COc1ccc(Nc2nccc3c(C(=O)Nc4cc(NC(=O)Nc5cccc(C(F)(F)F)c5)ccc4C)cccc23)nc1] |
| 21 | 1-((5-methoxypyridin-2-yl)amino)-N-(2-methyl-5-((3-(trifluoromethyl)phenyl)carbamoyl)phenyl)isoquinoline-5-carboxamide | 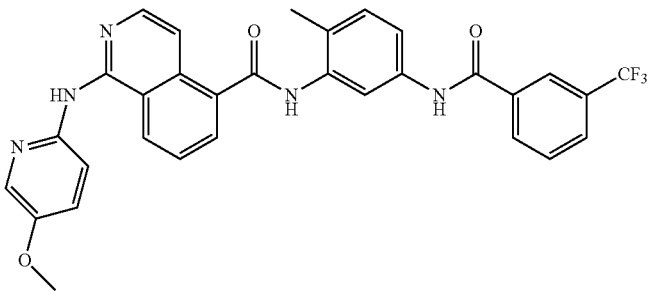 [SMILES: COc1ccc(Nc2nccc3c(C(=O)Nc4cc(NC(=O)c5cccc(C(F)(F)F)c5)ccc4C)cccc23)nc1] |

TABLE 1-continued

| Example | Name | Formula |
|---|---|---|
| 22 | N-(2-methyl-5-(3-(trifluoromethyl)benzamido)phenyl)isoquinoline-5-carboxamide | 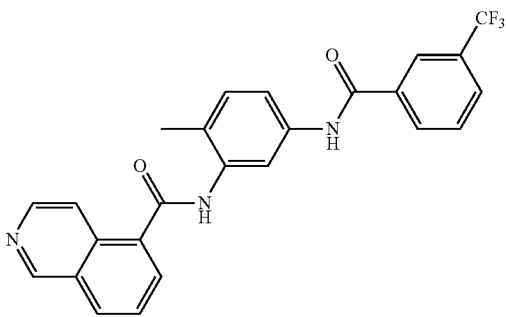 [SMILES: Cc1ccc(NC(=O)c2cccc(C(F)(F)F)c2)cc1NC(=O)c1cccc2cnccc12] |
| 23 | N-(1-((4-chlorophenyl)amino)-6-methylisoquinolin-5-yl)isoquinoline-5-carboxamide | 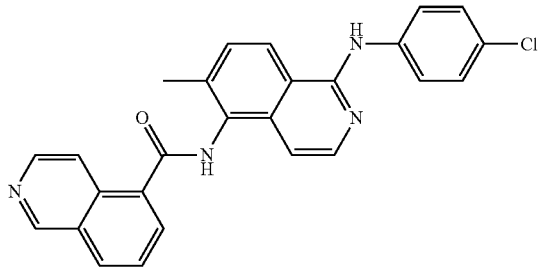 [SMILES: Cc1ccc2c(Nc3ccc(Cl)cc3)nccc2c1NC(=O)c1cccc2cnccc12] |

The compounds prepared in Examples were tested for biological assays as follows.

Experimental Example 1

Evaluation of the Inhibitory Activities of the Compounds Against C-Raf Kinase

The compounds prepared in Examples were tested for inhibitory activities against three subtypes of RAF, i.e. RAF1 Y340D Y341D, BRAF normal type and BRAF V600E, using Kinase Profiling Service (Invitrogen) according to the manufacturer's instructions. The levels of the inhibitory activities of the compounds against the enzymes were calculated as % inhibitory activities at various concentrations. Based on the % inhibitory activities, dose-response curves were plotted and $IC_{50}$ values were calculated using GraphPad Prism software. The $IC_{50}$ values of representative compounds against C-Raf are listed in Table 2, and Vemurafenib (PLX-4032, Roche) was used as a reference.

TABLE 2

| Example | C-Raf ($IC_{50}$, nM) |
|---|---|
| reference | 128 |
| 1 | 6.1 |
| 2 | 11 |
| 3 | 2.8 |
| 4 | 10.7 |
| 6 | 6.4 |
| 8 | 20.5 |
| 11 | 94.8 |
| 14 | 107.8 |

As shown in Table 2, the inventive compounds of formula (I) showed an excellent inhibitory activity against C-Raf protein kinases.

Experimental Example 2

Evaluation of the Inhibitory Activities of the Compounds Against Various Kinases In a similar manner to Experimental Example 1, the % inhibitory activity (concentration of the compound 1.0 μM) and the $IC_{50}$ values of the inventive compound of Example 1 against various kinases were obtained by using Kinase Profiling Service (Invitrogen) according to the manufacturer's instructions. The results are shown in Tables 3 and 4 below.

TABLE 3

| Protein kinase | Inhibitory activity at 1.0 μM (%) |
|---|---|
| VEGFR1 | 9% |
| FGFR4 | 7% |
| Tie-2 | 20% |
| c-Kit | 34% |
| CDK1 | 9% |
| CDK2 | 6% |
| PLK1 | −1% |
| PLK2 | 7% |
| PLK3 | 9% |
| Aurora A | 62% |
| Aurora B | 23% |

TABLE 4

| Protein kinase | Inhibitory activity ($IC_{50}$, nM) |
|---|---|
| B-Raf (WT) | 87 |
| B-Raf (V600E) | 61 |
| EGFR | >2,500 |
| Her-2 | >2,500 |
| PDGFR-α | 393 |
| PDGFR-β | 66 |
| VEGFR-2 | 261 |
| FGFR-1 | >2,500 |
| FGFR-2 | >2,500 |

TABLE 4-continued

| Protein kinase | Inhibitory activity (IC$_{50}$, nM) |
| --- | --- |
| FLT-3 | >2,500 |
| IGF-1R | >2,500 |
| Src | >2,500 |
| Abl | >2,500 |

As shown in Tables 3 and 4 above, the inventive compounds showed a selective inhibitory activity against Raf enzyme, PDGFR enzyme and VEGRF enzyme.

Experimental Example 3

Evaluation of Inhibition on Cell Proliferation of HepG2 (Hepatoma Carcinoma Cell)

The isoquinoline-5-carboxamide derivatives according to the present invention were tested for inhibitory activities on proliferation of aberrant cells at cellular levels as below.

HepG2 cell lines (ATCC #HB-8065™) were obtained from ATCC (American type culture collection; Rockville, Md.). HepG2 cell lines were incubated in a MEM medium supplemented with 10% FBS (Gibco) and 1% penicillin/streptomycin (Gibco) under 37° C., 5% CO$_2$ and 95% air. The carcinoma cells grown on the growth medium were transferred into a 96-well plate at a density of 5,000 cells/well (HepG2), and cultured for 18 hours or more. The cells were treated with 10 µM~0.1 nM of the test compounds, and cultured for 72 hours. Subsequently, the cells were fixed with 10% TCA (trichloroacetic acid) and stained with SRB (sulforhodamine B), and absorbance values were measured at 540 nm. Then, IC$_{50}$ values, i.e., the concentration of a compound to cause 50% reduction in proliferation of cancer cells, were calculated therefrom. The growth rates of cancer cells were calculated by Equation 1 or 2.

$$[(Ti-Tz)/(C-Tz)] \times 100 \text{ (in case } Ti>Tz) \quad \text{[Equation 1]}$$

$$[(Ti-Tz)/Tz] \times 100 \text{ (in case } Ti<Tz) \quad \text{[Equation 2]}$$

In Equations 1 and 2, 'Tz' refers to a the absorbance value measured in the cells just before the application of the test compound. 'C' refers to the absorbance value measured in the medium alone without the cells, and 'Ti' refers to the absorbance value measured in the cells treated with the test compounds.

IC$_{50}$ value is the concentration of the test compound when the value of Equation 1 is 50, which indicates the concentration of the test compound needed to reduce the growth of cancer cells to 50%. On each measurement, the test compounds were compared with a reference. Vemurafenib (PLX-4032) was used as a reference. The IC$_{50}$ values of each compound were measured and shown in Table 5.

TABLE 5

| Example | Inhibitory activities against HepG2 (IC$_{50}$, nM) |
| --- | --- |
| reference | >10,000 |
| 1 | 210 |
| 2 | 365 |
| 3 | 131 |

As evidenced above, the isoquinoline-5-carboxamide derivatives of the present invention having inhibitory activities against multiple protein kinases can selectively inhibit Raf kinase protein and other protein kinases, and thus can be used alone or in combination, for the prevention and treatment of diseases associated with aberrant cell growth, which are caused by overexpression of protein or overactivation of protein kinases, minimizing adverse side effects.

What is claimed is:

1. A compound selected from the group consisting of an isoquinoline-5-carboxamide of formula (I), a pharmaceutically acceptable salt, an isomer, a hydrate and a solvate thereof:

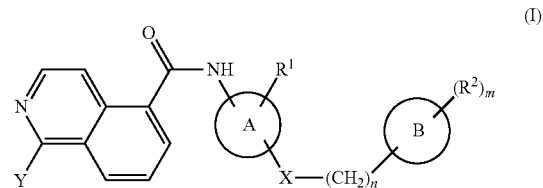

(I)

wherein,

A is $C_{6-10}$ aryl or $C_{5-10}$ heteroaryl;

B is $C_{6-10}$ aryl or $C_{5-10}$ heteroaryl;

X is —NH—, —C(O)NH—, —NHC(O)—, —NHC(O)NH—, —C(S)NH—, —NHC(S)—, —NHC(S)NH—, —NHSO$_2$— or —SO$_2$NH—;

Y is hydrogen, $C_{1-3}$ alkyl or NR$^3$R$^4$, wherein said R$^3$ and R$^4$ are each independently hydrogen, $C_{1-6}$ alkyl or —(CH$_2$)$_q$—Z—, wherein said Z is NR$^5$R$^6$, $C_{1-6}$ alkoxy, $C_{3-6}$ cycloalkyl, $C_{3-6}$ heterocycloalkyl, $C_{6-10}$ aryl or $C_{5-10}$ heteroaryl, wherein said R$^5$ and R$^6$ are each independently hydrogen, —NH$_2$, $C_{1-6}$ alkyl, $C_{1-6}$ alkoxy, $C_{3-6}$ cycloalkyl or $C_{3-6}$ heterocycloalkyl, said alkyl, alkoxy, cycloalkyl or heterocycloalkyl being unsubstituted or substituted with one or more halogen atoms, q is an integer ranging from 0 to 3;

R$^1$ is hydrogen, halogen, $C_{1-3}$ alkyl or $C_{1-3}$ alkoxy, wherein said alkyl or alkoxy is unsubstituted or substituted with one or more halogen atoms;

R$^2$ is hydrogen, halogen, —CF$_3$, —NO$_2$, —OH, $C_{1-6}$ alkoxy, $C_{1-6}$ alkyl, $C_{2-4}$ alkenyl, $C_{2-4}$ alkynyl, —NR$^7$R$^8$, —NHSO$_2$R$^9$, —SO$_2$R$^{10}$, —C(O)R$^{11}$, —NHC(O)R$^{12}$, —NHC(O)OR$^{13}$, $C_{3-6}$ cycloalkyl, $C_{3-6}$ heterocycloalkyl, $C_{6-10}$ aryl, $C_{6-10}$ aryloxy, $C_{5-10}$ heteroaryl or $C_{5-10}$ heteroaryloxy, wherein said R$^2$ is connected to B by —(CH$_2$)$_p$— or may be substituted with halogen, cyano, $C_{1-4}$ alkyl or $C_{1-4}$ alkylcarbonyl, wherein said R$^7$, R$^8$, R$^9$, R$^{10}$, R$^{11}$, R$^{12}$ and R$^{13}$ are each independently hydrogen, —NH$_2$, $C_{1-6}$ alkyl, $C_{1-6}$ alkoxy, $C_{3-6}$ cycloalkyl or $C_{3-6}$ heterocycloalkyl, said alkyl, alkoxy, cycloalkyl or heterocycloalkyl being unsubstituted or substituted with one or more halogen atoms, and p is 1 or 2;

m is an integer ranging from 0 to 5; and n is an integer ranging from 0 to 2.

2. The compound of claim 1, wherein A is phenyl or isoquinoline.

3. The compound of claim 1, wherein X is —NH—, —C(O)NH—, —NHC(O)— or —NHC(O)NH—.

4. The compound of claim 1, wherein Y is hydrogen, amino, —NHCH(CH₃)₃, or

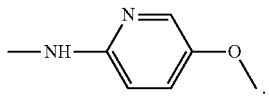

5. The compound of claim 1, wherein A is phenyl or isoquinoline; X is —NH—, —C(O)NH—, —NHC(O)— or —NHC(O)NH—; and Y is hydrogen, amino, —NHCH(CH₃)₃, or

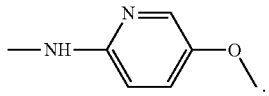

6. The compound of claim 1, wherein the isoquinoline-5-carboxamide of formula (I) is selected from the group consisting of:
1) 1-amino-N-(2-methyl-5-(3-(trifluoromethyl)benzamido)phenyl)isoquinoline-5-carboxamide;
2) 1-(t-butylamino)-N-(2-methyl-5-((3-(trifluoromethyl)phenyl)carbamoyl)phenyl)isoquinoline-5-carboxamide;
3) 1-amino-N-(2-methyl-5-((3-(trifluoromethyl)phenyl)carbamoyl)phenyl)isoquinoline-5-carboxamide;
4) 1-amino-N-(5-((4-chloro-3-(trifluoromethyl)phenyl)carbamoyl)-2-methylphenyl)isoquinoline-5-carboxamide;
5) 1-amino-N-(5-((3-(2-cyanopropan-2-yl)phenyl)carbamoyl)-2-methylphenyl)isoquinoline-5-carboxamide;
6) 1-(t-butylamino)-N-(5-((4-((4-ethylpiperazin-1-yl)methyl)-3-(trifluoromethyl)phenyl)carbamoyl)-2-methylphenyl)isoquinoline-5-carboxamide;
7) 1-amino-N-(5-((4-((4-ethylpiperazin-1-yl)methyl)-3-(trifluoromethyl)phenyl)carbamoyl)-2-methylphenyl)isoquinoline-5-carboxamide;
8) 1-(t-butylamino)-N-(2-methyl-5-(phenylcarbamoyl)phenyl)isoquinoline-5-carboxamide;
9) 1-amino-N-(2-methyl-5-((4-(trifluoromethyl)pyridin-2-yl)carbamoyl)phenyl)isoquinoline-5-carboxamide;
10) 1-amino-N-(5-((4,6-dimethylpyridin-2-yl)carbamoyl)-2-methylphenyl)isoquinoline-5-carboxamide;
11) 1-amino-N-(2-methyl-5-((3-(4-methyl-1H-imidazol-1-yl)-5-(trifluoromethyl)phenyl)carbamoyl)phenyl)isoquinoline-5-carboxamide;
12) 1-(t-butylamino)-N-(5-(3-(4-chloro-3-(trifluoromethyl)phenyl)ureido)-2-methylphenyl)isoquinoline-5-carboxamide;
13) 1-amino-N-(5-(3-(4-chloro-3-(trifluoromethyl)phenyl)ureido)-2-methylphenyl)isoquinoline-5-carboxamide;
14) 1-amino-N-(2-methyl-5-(3-(3-(trifluoromethyl)phenyl)ureido)phenyl)isoquinoline-5-carboxamide;
15) 1-(t-butylamino)-N-(5-(3-(2-fluoro-5-(trifluoromethyl)phenyl)ureido)-2-methylphenyl)isoquinoline-5-carboxamide;
16) 1-amino-N-(5-(3-(2-fluoro-5-(trifluoromethyl)phenyl)ureido)-2-methylphenyl)isoquinoline-5-carboxamide;
17) 1-amino-N-(3-((3-(trifluoromethyl)phenyl)carbamoyl)phenyl)isoquinoline-5-carboxamide;
18) 1-amino-N-(6-methyl-1-((3-(trifluoromethyl)phenyl)amino)isoquinolin-5-yl)isoquinoline-5-carboxamide;
19) 1-((5-methoxypyridin-2-yl)amino)-N-(2-methyl-5-(3-(trifluoromethyl)benzamido)phenyl)isoquinoline-5-carboxamide;
20) 1-((5-methoxypyridin-2-yl)amino)-N-(2-methyl-5-(3-(3-(trifluoromethyl)phenyl)ureido)phenyl)isoquinoline-5-carboxamide;
21) 1-((5-methoxypyridin-2-yl)amino)-N-(2-methyl-5-((3-(trifluoromethyl)phenyl)carbamoyl)phenyl)isoquinoline-5-carboxamide;
22) N-(2-methyl-5-(3-(trifluoromethyl)benzamido)phenyl)isoquinoline-5-carboxamide; and
23) N-(1-((4-chlorophenyl)amino)-6-methylisoquinolin-5-yl)isoquinoline-5-carboxamide.

7. A pharmaceutical composition comprising the compound of claim 1 as an active ingredient for the prevention or treatment of diseases associated with abnormal cell growth, which are caused by abnormal activation of protein kinases.

8. The pharmaceutical composition of claim 7, wherein said kinases are selected from the group consisting of A-RAF, B-RAF, C-RAF, PDGFR alpha, PDGFR beta, VEGRF and a combination thereof.

9. The pharmaceutical composition of claim 7, wherein said disease is selected from the group consisting of: gastric cancer, lung cancer, liver cancer, colorectal cancer, small intestine cancer, pancreatic cancer, brain cancer, bone cancer, melanoma, breast cancer, sclerosing adenosis, uterine cancer, cervical cancer, head and neck cancer, esophagus cancer, thyroid cancer, parathyroid cancer, renal cancer, sarcoma, prostate cancer, urethral cancer, bladder cancer, blood cancer, lymphoma, fibroadenoma, inflammation, diabetes, obesity, psoriasis, rheumatoid arthritis, hemangioma, acute or chronic kidney disease, coronary restenosis, autoimmune diseases, asthma, neurodegenerative diseases, acute infection and ocular diseases caused by angiogenesis.

10. A method for treatment of a disease associated with abnormal cell growth, which is caused by abnormal activation of a protein kinase, which comprises administering to the subject in need thereof the compound of claim 1.

11. A method for treating a disease associated with abnormal cell growth, which is caused by abnormal activation of a protein kinase, which comprises administering to the subject in need thereof the compound of claim 6.

12. The method of claim 10, wherein the protein kinase is selected from the group consisting of A-RAF, B-RAF, C-RAF, PDGFR alpha, PDGFR beta, VEGRF and a combination thereof.

13. The method of claim 11, wherein the protein kinase is selected from the group consisting of A-RAF, B-RAF, C-RAF, PDGFR alpha, PDGFR beta, VEGRF and a combination thereof.

* * * * *